United States Patent
Matsumoto et al.

(10) Patent No.: US 10,757,972 B2
(45) Date of Patent: Sep. 1, 2020

(54) NON-BURNING TYPE FLAVOR INHALER AND PACKAGE

(71) Applicant: JAPAN TOBACCO INC., Tokyo (JP)

(72) Inventors: Hirofumi Matsumoto, Tokyo (JP); Akihiko Suzuki, Tokyo (JP); Manabu Takeuchi, Tokyo (JP); Takuma Nakano, Tokyo (JP); Masafumi Tarora, Tokyo (JP); Manabu Yamada, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 0 days.

(21) Appl. No.: 16/450,570

(22) Filed: Jun. 24, 2019

(65) Prior Publication Data

US 2019/0307166 A1    Oct. 10, 2019

Related U.S. Application Data

(63) Continuation of application No. 15/590,346, filed on May 9, 2017, now Pat. No. 10,342,258, which is a
(Continued)

(30) Foreign Application Priority Data

Nov. 10, 2014   (WO) .................. PCT/JP2014/079777

(51) Int. Cl.
    A24F 13/00      (2006.01)
    A24F 17/00      (2006.01)
    (Continued)

(52) U.S. Cl.
    CPC ............ *A24F 47/002* (2013.01); *A24F 15/08* (2013.01); *A24F 47/00* (2013.01); *A61M 11/003* (2014.02);
    (Continued)

(58) Field of Classification Search
    CPC .................................................... A24F 47/008
    (Continued)

(56) References Cited

U.S. PATENT DOCUMENTS

6,040,560 A * 3/2000 Fleischhauer ......... A24F 47/008
                                                      128/202.21
9,067,029 B2   6/2015 Yamada et al.
(Continued)

FOREIGN PATENT DOCUMENTS

EA      201692211 A1    2/2017
EP        3138424 A1    3/2017
(Continued)

OTHER PUBLICATIONS

Japanese Office Action, dated Oct. 11, 2019, for Japanese Application No. 2019-111861, along with an English translation.
(Continued)

*Primary Examiner* — Abdullah A Riyami
*Assistant Examiner* — Thang H Nguyen
(74) *Attorney, Agent, or Firm* — Birch, Stewart, Kolasch & Birch, LLP

(57) ABSTRACT

A cartridge for a non-burning type flavor inhaler including a flow path forming body having a shape extending along a predetermined direction to form an aerosol flow path, an outer frame having a shape extending along the predetermined direction to accommodate the flow path forming body, a reservoir that is configured to retain an aerosol source, is positioned on the periphery of the flow path forming body in a cross section orthogonal to the predetermined direction and is positioned in a gap between the flow path forming body and the outer frame and an end cap that closes the gap from the downstream side, wherein an outer edge of the end cap contacts an inner wall surface of the outer frame in the cross section orthogonal to the predeter-
(Continued)

UPSTREAM ←——→ DOWNSTREAM
PREDETERMINED DIRECTION A mined direction and wherein an inner edge of the end cap is positioned between the outer edge of the flow path forming body and the inner edge of the flow path forming body in the cross section orthogonal to the predetermined direction.

7 Claims, 20 Drawing Sheets

Related U.S. Application Data continuation of application No. PCT/JP2015/081047, filed on Nov. 4, 2015.

(51) Int. Cl.
*A24F 25/00* (2006.01)
*A24F 47/00* (2020.01)
*A61M 11/00* (2006.01)
*A61M 11/06* (2006.01)
*A24F 15/08* (2006.01)
*A24F 15/00* (2020.01)
*A61M 15/06* (2006.01)

(52) U.S. Cl.
CPC ............ *A61M 11/065* (2014.02); *A24F 15/00* (2013.01); *A61M 11/001* (2014.02); *A61M 11/06* (2013.01); *A61M 15/06* (2013.01)

(58) Field of Classification Search
USPC ........................................................ 131/329
See application file for complete search history.

(56) References Cited

U.S. PATENT DOCUMENTS

| | | | | |
|---|---|---|---|---|
| 10,357,061 B2* | 7/2019 | Li | .......................... | A61M 15/06 |
| 2011/0265806 A1* | 11/2011 | Alarcon | .................. | A24F 47/00 |
| | | | | 131/273 |
| 2013/0213419 A1* | 8/2013 | Tucker | ................... | H05B 3/141 |
| | | | | 131/328 |
| 2013/0228191 A1* | 9/2013 | Newton | ................ | A24F 47/008 |
| | | | | 131/329 |
| 2013/0340775 A1 | 12/2013 | Juster et al. | | |
| 2014/0060554 A1* | 3/2014 | Collett | ................... | H05B 3/265 |
| | | | | 131/328 |
| 2014/0096782 A1* | 4/2014 | Ampolini | .............. | A24F 47/008 |
| | | | | 131/328 |
| 2014/0209105 A1* | 7/2014 | Sears | .................... | A24F 47/008 |
| | | | | 131/328 |
| 2014/0238423 A1* | 8/2014 | Tucker | .................. | A24F 47/008 |
| | | | | 131/328 |
| 2014/0238424 A1* | 8/2014 | Macko | .................. | A24F 47/008 |
| | | | | 131/328 |
| 2015/0122276 A1 | 5/2015 | Johnson et al. | | |
| 2015/0224268 A1* | 8/2015 | Henry | .................... | G06Q 50/01 |
| | | | | 128/202.21 |
| 2015/0245662 A1* | 9/2015 | Memari | ............... | H05K 999/00 |
| | | | | 131/328 |
| 2015/0333561 A1* | 11/2015 | Alarcon | .................. | H02J 50/10 |
| | | | | 131/329 |
| 2016/0007652 A1* | 1/2016 | Taluskie | ............... | A61M 11/041 |
| | | | | 131/328 |
| 2017/0042251 A1* | 2/2017 | Yamada | ............... | A61M 15/003 |
| 2017/0246407 A1* | 8/2017 | Matsumoto | ........... | A24F 47/002 |
| 2017/0295847 A1* | 10/2017 | Liu | ......................... | H05B 3/44 |
| 2018/0049475 A1* | 2/2018 | Memari | ............... | H05K 999/00 |

FOREIGN PATENT DOCUMENTS

| | | | |
|---|---|---|---|
| GB | 2461008 A | | 12/2009 |
| JP | 2001-502542 A | | 2/2001 |
| JP | 2011-87569 A | | 5/2011 |
| JP | 2013-150593 A | | 8/2013 |
| KR | 10-0831535 B1 | | 5/2008 |
| KR | 10-1076144 B1 | | 10/2011 |
| KR | 10-2013-0046826 A | | 5/2013 |
| KR | 10-2013-0052119 A | | 5/2013 |
| TW | 201340894 A | | 10/2013 |
| WO | WO 2012/085205 A1 | | 6/2012 |
| WO | WO 2013/060743 A2 | | 5/2013 |
| WO | WO 2013/116558 A1 | | 8/2013 |
| WO | WO 2014/066730 A1 | | 5/2014 |
| WO | WO 2014/110119 A1 | | 7/2014 |
| WO | WO 2014/157463 A1 | | 10/2014 |

OTHER PUBLICATIONS

Korean Office Action, dated Oct. 1 , 2019, for Korean Application No. 10-2019-7026364, along with an English translation.
Australian Examination Report for Australian Application No. 2015347931, dated May 25, 2018.
Eurasian Office Action, dated Aug. 6, 2018, for Eurasian Application No. 201791039 as well as an English machine translation.
Extended European Search Report, dated Jun. 21, 2018, for corresponding European Application No. 15858446.6.
International Search Report, issued in PCT/JP2015/081047, PCT/ISA/210, dated Feb. 2, 2016.
Japanese Office Action dated Feb. 7, 2019, for the corresponding Japanese patent application No. 2018-208053, with English translation.
Japanese Office Action, dated Aug. 7, 2018, for Japanese Application No. 2016-558996 as well as an English machine translation.
Japanese Office Action, dated Mar. 6, 2018, for Japanese Application No. 2016-558996, as well as an English machine translation.
Korean Office Action for Korean Application No. 10-2017-7014599, dated Oct. 29, 2018, with English translation.
Korean Office Action, dated Apr. 26, 2018, for Korean Application No. 10-2017-7014599, as well as an English translation.
Taiwanese Office Action dated Oct. 12, 2017, for Taiwanese Application No. 104136825, with English translation.
Taiwanese Office Action for Taiwanese Application No. 104136825, dated Jun. 6, 2017, including an English translation.

\* cited by examiner

UPSTREAM ←PREDETERMINED DIRECTION A→ DOWNSTREAM

UPSTREAM ← PREDETERMINED DIRECTION A → DOWNSTREAM

UPSTREAM  ←PREDETERMINED→  DOWNSTREAM
            DIRECTION A

NON-BURNING TYPE FLAVOR INHALER AND PACKAGE

CROSS-REFERENCE TO RELATED APPLICATIONS

This application is a Continuation of U.S. patent application Ser. No. 15/590,346 filed on May 9, 2017, which is a Continuation of PCT International Application No. PCT/JP2015/081047 filed on Nov. 4, 2015, which claims priority under 35 U.S.C. § 119(a) to Patent Application No. PCT/JP2014/079777 filed in Japan on Nov. 10, 2014, all of which are hereby expressly incorporated by reference into the present application.

TECHNICAL FIELD

The present invention relates to a non-burning type flavor inhaler provided with a second cartridge and a first cartridge, and a package.

BACKGROUND ART

Known is a non-burning type flavor inhaler that atomizes an aerosol source using power supplied from a battery (for example, Patent Document 1).

For example, the non-burning type flavor inhaler is provided with a power source unit having at least a battery, a first cartridge having at least an aerosol source and an atomizer that atomizes the aerosol source, and a second cartridge having at least a flavor source. The second cartridge and the first cartridge are replaceable.

PRIOR ART DOCUMENT

Patent Document

Patent Document 1: WO 2013/116558

SUMMARY OF THE INVENTION

A first feature is summarized as a non-burning type flavor inhaler comprising: a power source unit including at least a battery; a first cartridge including at least an aerosol source and an atomizer configured to atomize the aerosol source without burning using power supplied from the battery; a second cartridge including at least a flavor source and imparts flavor to the aerosol by letting the aerosol atomized by the atomizer pass through; and a controller configured to control a notification unit to notify a replacement timing of the second cartridge in response to detection of the replacement timing of the second cartridge.

A second feature according to the first feature is summarized as that the controller controls the notification unit to notify a replacement timing of the first cartridge according to detection of the replacement timing of the first cartridge, and the controller detects the replacement timing of the first cartridge based on the number of replacement times of the second cartridge.

A third feature according to the first feature or the second feature is summarized as that the controller detects the replacement timing of the second cartridge based on the number of puff actions or an energization time of the atomizer.

A fourth feature according to the third feature is summarized as that the controller has a counter configured to count the number of puff actions or the energization time of the atomizer, and the controller detects the replacement timing of the second cartridge and resets the count value of the counter, when a count value of the counter reaches a predetermined value.

A fifth feature according to the third feature is summarized as that the controller has a counter configured to count the number of puff actions or the energization time of the atomizer, the controller detects the replacement timing of the second cartridge when a count value of the counter reaches the predetermined value, and the controller resets the count value of the counter by a predetermined operation of a user.

A sixth feature according to any one of the first feature to the fifth feature is summarized as that the controller controls the notification unit to notify a replacement timing of the battery or a charging timing of the battery in response to detection of the replacement timing of the battery or the charging timing of the battery.

A seventh feature according to the sixth feature is summarized as that the controller detects the replacement timing of the battery or the charging timing of the battery based on output voltage of the battery.

An eighth feature according to the fourth feature or the fifth feature is summarized as that the controller stops power supply from the battery to the atomizer from when a count value of the counter reaches a predetermined value until when the count value is reset.

A ninth feature according to the first feature is summarized as that the controller has a first counter and a second counter as a counter configured to count the number of puff actions or the energization time of the atomizer, the controller detects the replacement timing of the second cartridge when a count value of the first counter reaches a first predetermined value, the controller detects the replacement timing of the first cartridge when a count value of the second counter reaches a second predetermined value, and the second predetermined value is an integral multiple of the first predetermined value.

A tenth feature according to the second feature is summarized as that the controller has a counter configured to count a number of replacement times of the second cartridge, and the controller detects the replacement timing of the first cartridge when a count value of the counter reaches a predetermined value.

An eleventh feature according to any one of the first feature to the tenth feature is summarized as that the controller detects the replacement timing of the second cartridge based on the number of puff actions or an energization time, the controller outputs to the battery a predetermined instruction as the instruction to the battery, the predetermined instruction instructing the battery to make the aerosol amount, atomized by the atomizer, falls in a desired range, the controller stops power supply from the battery to the atomizer when a predetermined period from a start of power supply to the atomizer has elapsed, and the predetermined period is shorter than an upper limit value of a standard puff period derived from statistics of a puff period of a user.

A twelfth feature according to any one of the first feature to the eleventh feature is summarized as that the controller modifies the predetermined instruction with a reduction of an accumulated amount in the battery such that the aerosol amount atomized by the atomizer falls in the desired range.

A thirteenth feature according to any one of the first feature to the twelfth feature is summarized as that the controller performs a detection process to detect the replacement timing of the second cartridge when power supply from the battery to the atomizer is stopped.

A fourteenth feature according to the thirteenth feature is summarized as that the controller performs the detection process from stopping of the power supply from the battery to the atomizer until a determination period has elapsed.

A fifteenth feature according to the fourteenth feature is summarized as that the controller controls the notification unit to notify the replacement timing of the second cartridge from stopping of the power supply from the battery to the atomizer until the determination period has elapsed when the replacement timing of the second cartridge is detected in the detection process.

A sixteenth feature according to the fourteenth feature or the fifteenth feature is summarized as that the controller performs the detection process until the power supply from the battery to the atomizer starts in response to the start of a puff action when the puff action starts from stopping of the power supply from the battery to the atomizer until the detection process performed.

A seventeenth feature according to any one of the thirteenth feature to the sixteenth feature is summarized as that the controller performs the detection process when the power supply from the battery to the atomizer is stopped along with a detection of an end of the puff action.

An eighteenth feature according to any one of the thirteenth feature to the sixteenth feature is summarized as that the controller performs the detection process when the power supply from the battery to the atomizer is stopped along with elapse of a predetermined period from the start of power supply to the atomizer.

A nineteenth feature is summarized as a package used for the non-burning type flavor inhaler according to any one of the first feature to the eighteenth feature, comprising: a first cartridge including at least an aerosol source and an atomizer configured to atomize the aerosol source without burning; and one or more second cartridges each including at least a flavor source, wherein the number of the one or more second cartridges is determined according to the lifespan of the first cartridge.

A twentieth feature according to the nineteenth feature is summarized as that a permissible puff number or a permissible energization time is determined for the first cartridge, the permissible puff number being the number of puff actions permissible for the first cartridge, the permissible energization time being the energization time permissible for the first cartridge, a timing at which the number of puff actions or the energization time of the atomizer reaches a predetermined value is the replacement timing of the second cartridge, and the number of the second cartridges is an integral part of a quotient obtained by dividing the permissible puff number or the permissible energization time i by the predetermined value.

A twenty-first feature according to the nineteenth feature is summarized as that a timing at which the number of puff actions or the energization time of the atomizer reaches a first predetermined value is the replacement timing of the second cartridge, a timing at which the number of puff actions or the energization time of the atomizer reaches a second predetermined value is the replacement timing of the first cartridge, and the second predetermined value is an integral multiple of the first predetermined value.

In the fourteenth feature to the sixteenth feature, the determination period may be a period that is assumed to be shorter than a period from the end of a current puff action until a subsequent puff action starts. As the determination period, for example, it is possible to use a period such as three seconds, or preferably one second.

DESCRIPTION OF THE EMBODIMENT

Figure 1:
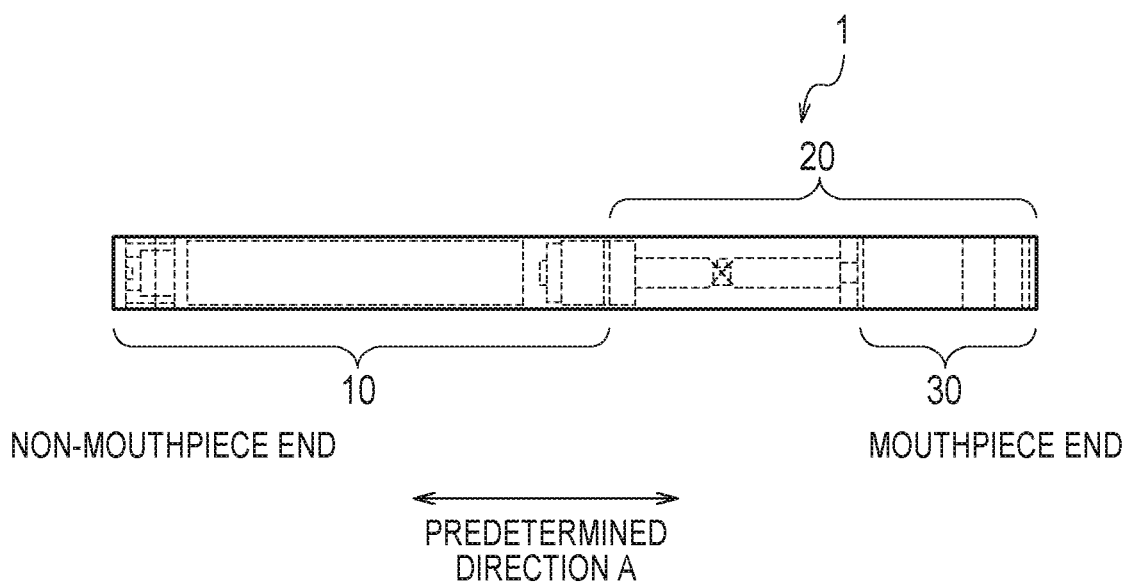
FIG. 1 is a cross-sectional view illustrating a non-burning type flavor inhaler 1 according to an embodiment.

Hereinafter, embodiments of the present invention will be described. In the following description of the drawings, the same or similar reference numerals denote the same or similar parts. It should be noted that the drawings are schematic, and the ratios of dimensions and the like may be different from the actual ones.

Therefore, specific dimensions and the like may be determined by referring to the following description. Of course, the drawings may include the parts having different dimensions and ratios.

[Overview of Disclosure]

As a result of extensive studies, the inventors found that the lifespan of the second cartridge is different from the lifespan of the first cartridge.

On the based on such new findings, with reference to the non-burning type flavor inhaler mentioned in the background art, in the non-burning type flavor inhaler described above, a replacement timing of the first cartridge or a replacement timing of the second cartridge is not notified to the user, therefore convenience of the user is impaired.

A non-burning type flavor inhaler according to the overview of disclosure comprises: a power source unit including at least a battery; a first cartridge including at least an aerosol source and an atomizer configured to atomize the aerosol source without burning using power supplied from the battery; a second cartridge including at least a flavor source and imparts flavor to the aerosol by letting the aerosol atomized by the atomizer pass through; and a controller configured to control a notification unit to notify a replacement timing of the second cartridge in response to detection of the replacement timing of the second cartridge.

In the overview of disclosure, the controller controls the notification unit to notify the replacement timing of the second cartridge in response to the detection of the replacement timing of the second cartridge. Accordingly, it is possible for the user to easily ascertain the replacement timing of the second cartridge.

Embodiment (Non-Burning Type Flavor Inhaler)

Figure 2:
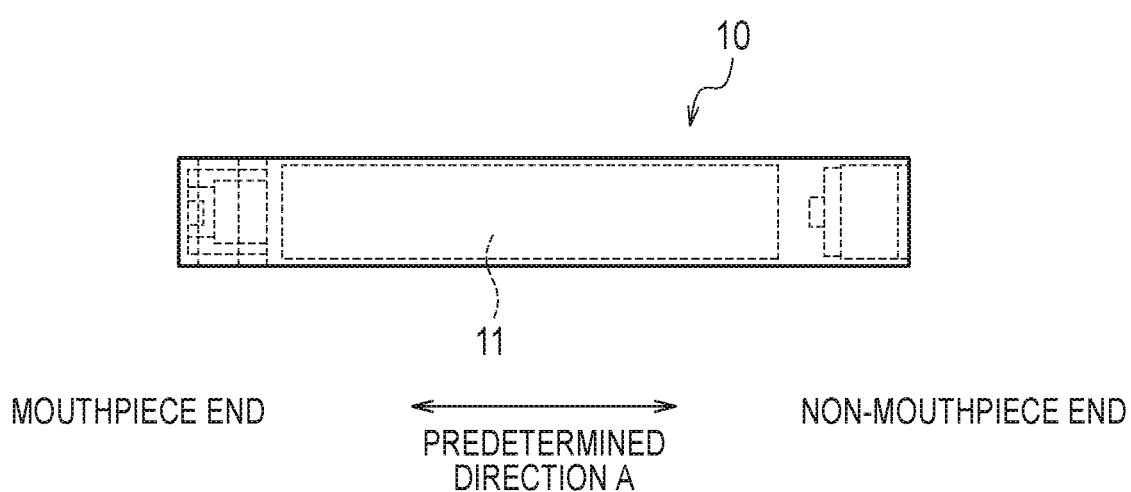
FIG. 2 is a cross-sectional view illustrating a power source unit 10 according to the embodiment.
Figure 3:
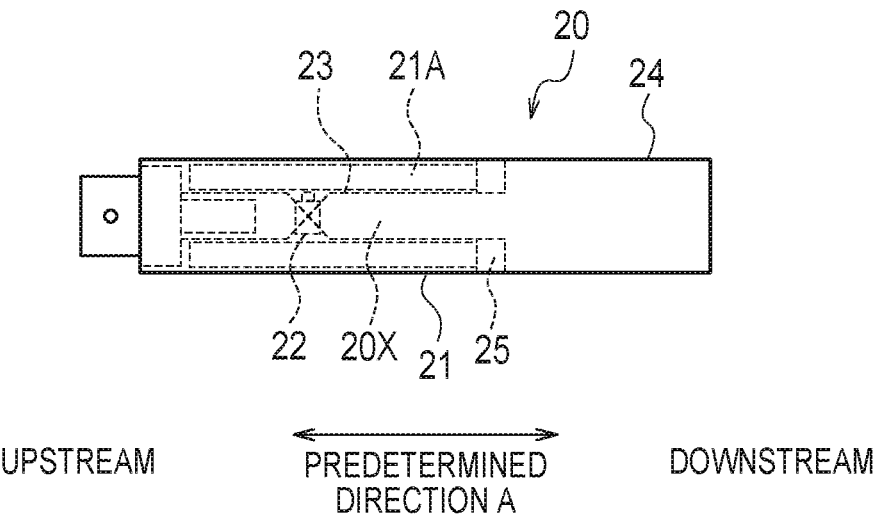
FIG. 3 is a cross-sectional view illustrating a first cartridge 20 according to the embodiment.
Figure 4:
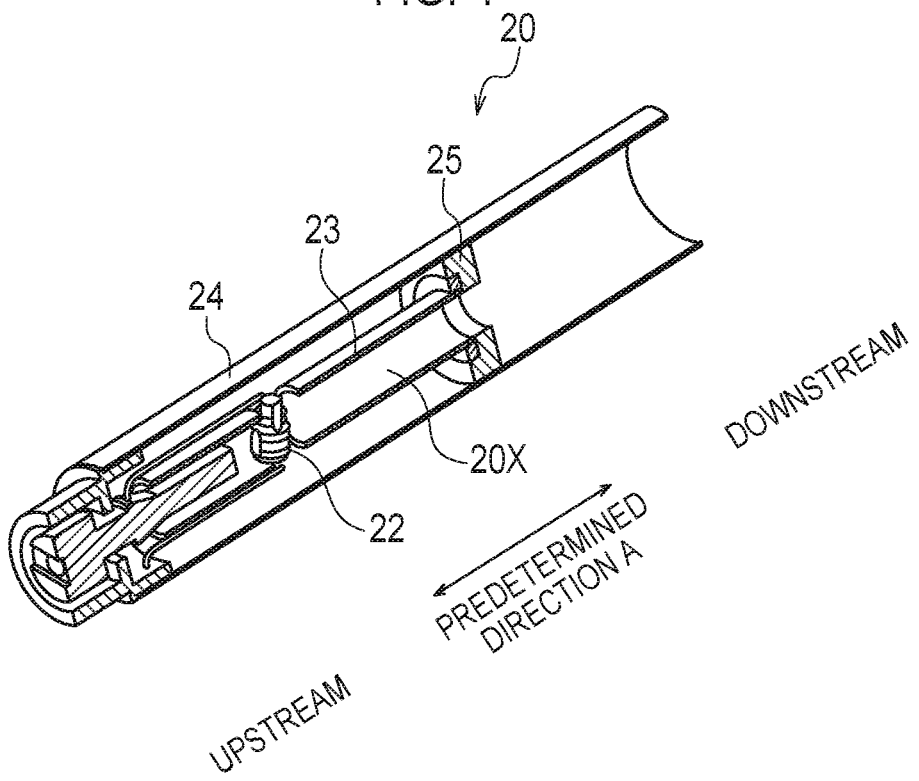
FIG. 4 is a diagram illustrating an internal structure of the first cartridge 20 according to the embodiment.
Figure 5:
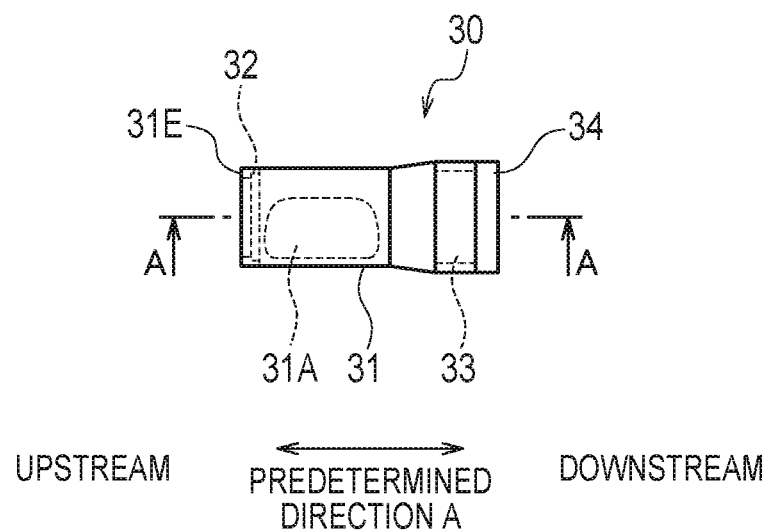
FIG. 5 is a cross-sectional view illustrating a second cartridge 30 according to the embodiment.
Figure 6:
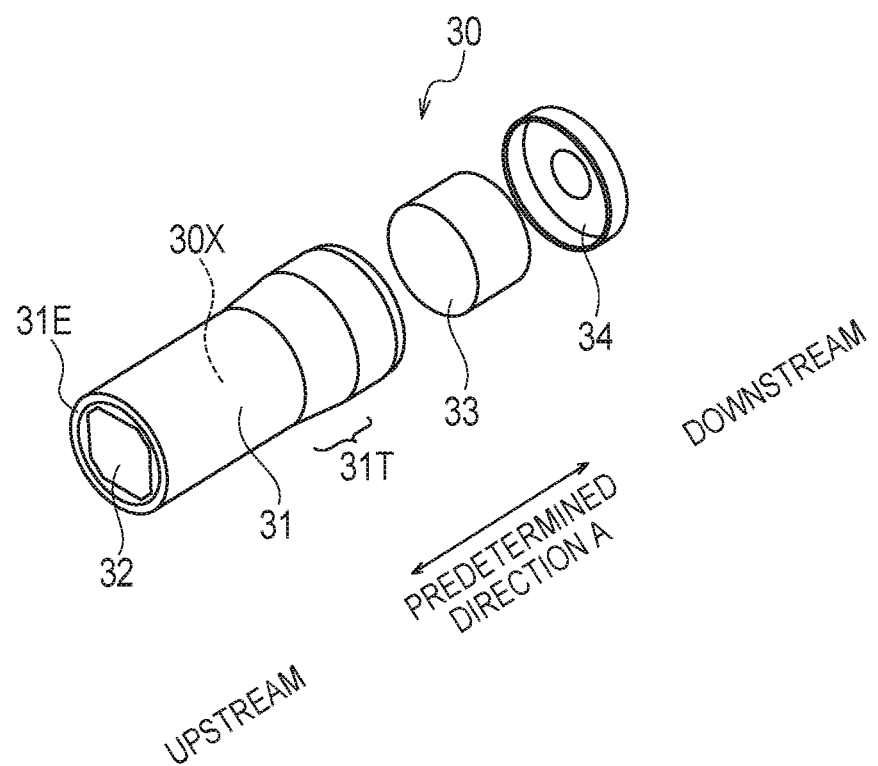
FIG. 6 is an exploded perspective view of the second cartridge 30 according to the embodiment.
Figure 7:
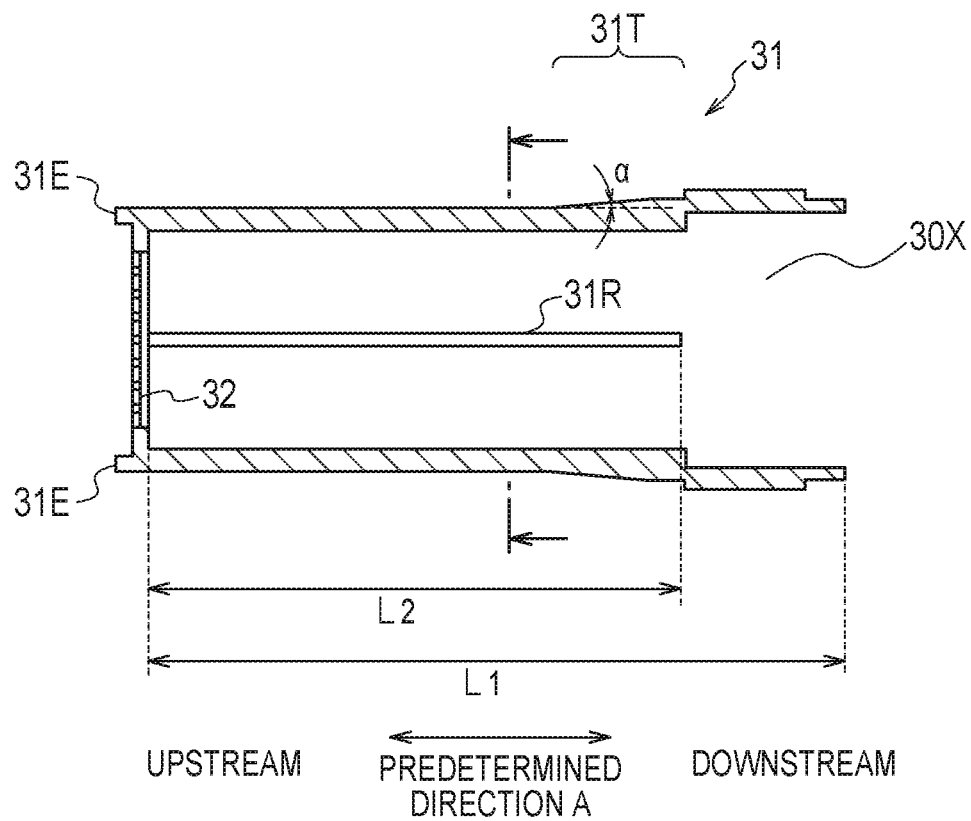
FIG. 7 is a cross-sectional view (cross-sectional view taken along A-A illustrated in FIG. 5) illustrating a flavor source container 31 according to the embodiment.
Figure 8:
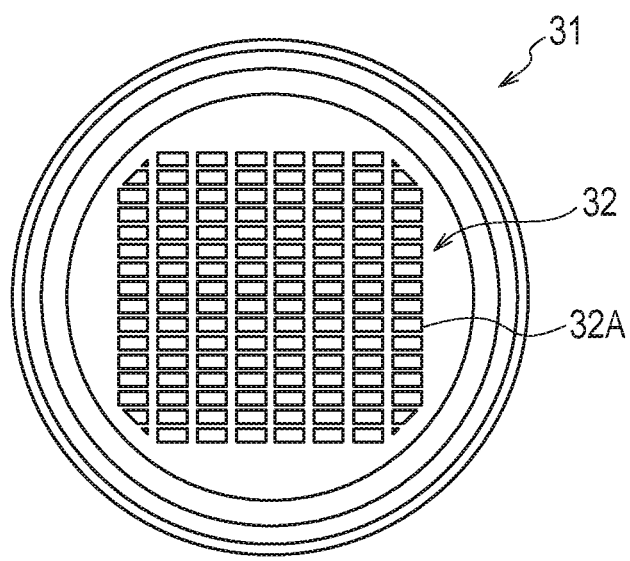
FIG. 8 is a cross-sectional view (cross-sectional view taken along B-B illustrated in FIG. 7) illustrating the flavor source container 31 according to the embodiment.

A non-burning type flavor inhaler according to an embodiment will be described below. FIG. 1 is a cross-sectional view illustrating a non-burning type flavor inhaler 1 according to the embodiment. FIG. 2 is a cross-sectional view illustrating a power source unit 10 according to the embodiment. FIG. 3 is a cross-sectional view illustrating a first cartridge 20 according to the embodiment. FIG. 4 is a diagram illustrating an internal structure of the first cartridge 20 according to the embodiment. It should be noted that a reservoir 21 that will be described later is omitted from FIG. 4. FIG. 5 is a side view illustrating a second cartridge 30 according to the embodiment. FIG. 6 is an exploded perspective view of the second cartridge 30 according to the embodiment. FIG. 7 is a cross-sectional view (cross-sectional view taken along A-A illustrated in FIG. 5) illustrating a flavor source container 31 according to the embodiment. FIG. 8 is a cross-sectional view (cross-sectional view taken along B-B illustrated in FIG. 7) illustrating the flavor source container 31 according to the embodiment. It should be noted that a flavor source 31A that will be described later is omitted from FIG. 6.

As illustrated in FIG. 1, the non-burning type flavor inhaler 1 has a shape extending in a predetermined direction A from a non-mouthpiece end toward a mouthpiece end. The non-burning type flavor inhaler 1 is an instrument for inhaling flavor without burning.

Specifically, the non-burning type flavor inhaler 1 has the power source unit 10, the first cartridge 20, and the second cartridge 30. The first cartridge 20 is attachable to and detachable from the power source unit 10, and the second cartridge 30 is attachable to and detachable from the first cartridge 20. In other words, the first cartridge 20 and the second cartridge 30 are each replaceable.

As illustrated in FIG. 2, the power source unit 10 has a shape extending along the predetermined direction A, and has at least a battery 11. The battery 11 may be a disposable battery and may be a rechargeable battery. An initial value of output voltage of the battery 11 is preferably in a range of from 1.2 to 4.2 V. In addition, the battery capacity of the battery 11 is preferably in a range of from 100 to 1000 mAh.

As illustrated in FIG. 3 and FIG. 4, the first cartridge 20 has a shape extending along the predetermined direction A. The first cartridge 20 has a reservoir 21, an atomizer 22, a flow path forming body 23, an outer frame 24, and an end cap 25. The first cartridge 20 has a first flow path 20X provided on the downstream than the atomizer 22 as an aerosol flow path extending along the predetermined direction A. It should be noted that in the aerosol flow path, a side near to the atomizer 22 is referred to as upstream and a side away from the atomizer 22 is referred to as downstream.

The reservoir 21 retains an aerosol source 21A. The reservoir 21 is positioned on the periphery of the flow path forming body 23 in a cross section orthogonal to the first flow path 20X (predetermined direction A). In the embodiment, the reservoir 21 is positioned in a gap between the flow path forming body 23 and the outer frame 24. For example, the reservoir 21 is constituted by a porous body such as a resin web or cotton. However, the reservoir 21 may be constituted by a tank that accommodates the liquid aerosol source 21A. The aerosol source 21A includes a liquid such as glycerin or propylene glycol.

The atomizer 22 atomizes the aerosol source 21A not accompanying burning caused by power supplied from the battery 11. In the embodiment, the atomizer 22 is constituted by a heating wire (coil) wound at a predetermined pitch, and preferably the atomizer 22 is constituted by a heating wire that has a resistance value in the range of from 1.0 to 3.0Ω. The predetermined pitch is a value or more such that the heating wires do not contact, and preferably is a small value. For example, the predetermined pitch is preferably 0.40 mm or less. The predetermined pitch is preferably fixed to stabilize atomization of the aerosol source 21A. Note that, the predetermined pitch is an interval in the center of heating wires that are adjacent to each other.

The flow path forming body 23 has a shape extending along the predetermined direction A. The flow path forming body 23 has a cylindrical shape that forms the first flow path 20X extending along the predetermined direction A.

The outer frame 24 has a shape extending along the predetermined direction A. The outer frame 24 has a cylindrical shape that accommodates the flow path forming body 23. In the embodiment, the outer frame 24 accommodates a part of the second cartridge 30 while extending to the downstream side than the end cap 25.

The end cap 25 is a cap that closes a gap between the flow path forming body 23 and the outer frame 24 from the downstream side. The end cap 25 suppresses a situation such that the aerosol source 21A retained in the reservoir 21 leaks to the second cartridge 30 side.

As illustrated in FIG. 5 and FIG. 6, the second cartridge 30 has at least the flavor source 31A. The second cartridge 30 is mounted in the non-burning type flavor inhaler 1. In the embodiment, the second cartridge 30 is connected to the first cartridge 20. More particularly, a part of the second cartridge 30 is accommodated in the outer frame 24 of the first cartridge 20 as described above.

The second cartridge 30 has a shape extending along the predetermined direction A. The second cartridge 30 has the flavor source container 31, a mesh body 32, a filter 33, and a cap 34. The second cartridge 30 has a second flow path 30X provided on the downstream than the first flow path 20X as the aerosol flow path.

The second cartridge 30 imparts flavor to the aerosol by letting the aerosol atomized by the atomizer 22 pass through. Here, in the embodiment, it should be noted that it is possible to impart flavor to the aerosol without heating the flavor source 31A. It should be noted that the aerosol is not practically generated from the flavor source 31A.

In the predetermined direction A, preferably a maximum size of the second cartridge 30 is 40 mm or less. Furthermore, in the predetermined direction A, preferably the maximum size of the second cartridge 30 is 25 mm or less. Meanwhile, in the predetermined direction A, preferably a minimum size of the second cartridge 30 is 5 mm or more. Furthermore, in the predetermined direction A, preferably the minimum size of the second cartridge 30 is 1 mm or more. In a direction orthogonal to the predetermined direction A, preferably the maximum size of the second cartridge 30 is 20 mm or less. Furthermore, in the direction orthogonal to the predetermined direction A, preferably the maximum size of the second cartridge 30 is 10 mm or less. Meanwhile, in the direction orthogonal to the predetermined direction A, preferably the minimum size of the second cartridge 30 is 3 mm or more. Furthermore, in the direction orthogonal to the predetermined direction A, preferably the minimum size of the second cartridge 30 is 1 mm or more.

The flavor source container 31 has a cylindrical shape and forms the second flow path 30X extending along the predetermined direction A. The flavor source container 31 accommodates the flavor source 31A. The flavor source 31A that imparts flavor to the aerosol is accommodated in the second flow path 30X. Here, in a cross section orthogonal to the aerosol flow path (predetermined direction A), preferably the size of the first flow path 20X is small to secure volume of the reservoir 21 that retains the aerosol source 21A. Accordingly, in a case in which the second cartridge 30 is accommodated in the outer frame 24 that has a fixed cross-sectional area across the aerosol flow path (predetermined direction A), as a result, the size of the second flow path 30X tends to be larger than the size of the first flow path 20X described above.

The flavor source 31A is constituted by raw material pieces that impart flavor to the aerosol generated by the non-burning type flavor inhaler 1. Preferably the lower limit of the size of the raw material pieces is from 0.2 to 1.2 mm. Furthermore, preferably the lower limit of the size of the raw material pieces is from 0.2 to 0.7 mm. The smaller the size of the raw material pieces included in the flavor source 31A, the more the specific surface area increases, therefore a flavor component tends to be released from the raw material pieces included in the flavor source 31A. It is possible to use shredded tobacco or a molded body in which a tobacco raw material is granularly formed as the raw material pieces included in the flavor source 31A. The flavor source 31A may be constituted by a plant other than tobacco (for example, mint and herbs). Flavorings such as menthol may be added to the flavor source 31A.

Here, for example, the raw material pieces included in the flavor source 31A are obtained by sieving compliant with JIS Z 8815 using a stainless steel sieve compliant with JIS Z 8801. For example, the raw material pieces that pass through the stainless steel sieve that has sieve openings of 0.71 mm are obtained by sieving the raw material pieces over 20 minutes by a drying and mechanical shaking method using the stainless steel sieve that has the sieve openings of 0.71 mm. Subsequently, the raw material pieces that pass through the stainless steel sieve that has sieve openings of 0.212 mm are removed by sieving the raw material pieces over 20 minutes by the drying and mechanical shaking method using the stainless steel sieve that has the sieve openings of 0.212 mm. That is, the raw material pieces included in the flavor source 31A are raw material pieces that pass through the stainless steel sieve (sieve openings=0.71 mm) that regulates the upper limit and do not pass through the stainless steel sieve (sieve openings=0.212 mm) that regulates the lower limit. Accordingly, in the embodiment, the lower limit of the size of the raw material pieces included in the flavor source 31A is defined by the sieve openings of the stainless steel sieve that regulates the lower limit. Note that, the upper limit of the size of the raw material pieces included in the flavor source 31A is defined by the sieve openings of the stainless steel sieve that regulates the upper limit.

In the embodiment, as illustrated in FIG. 6 and FIG. 7, preferably the flavor source container 31 has a protruding portion 31E that protrudes to the upstream side (in the embodiment, the flow path forming body 23 or the end cap 25 side) from an outer edge of an upstream end portion (here, the mesh body 32) of the flavor source container 31 in a cross section orthogonal to the aerosol flow path (predetermined direction A). The protruding portion 31E may be continuously provided along the outer edge of the upstream end portion (here, the mesh body 32) of the flavor source container 31 and may be intermittently provided along the outer edge of the flavor source container 31. Note that, when there is a gap between the outer frame 24 and the flavor source container 31, preferably the protruding portion 31E is continuously provided along the outer edge of the upstream end portion (here, the mesh body 32) of the flavor source container 31. Thereby, it is possible to suppress retention of aerosol in the gap formed in the upstream part of a taper part 31T.

In the embodiment, as illustrated in FIG. 6 and FIG. 7, preferably an outer wall surface of the flavor source container 31 includes the taper part 31T that becomes wide from the upstream to the downstream. The taper part 31T may be contained in a part of the outer wall surface of the flavor source container 31. For example, a taper angle α of the taper part 31T is approximately 5 degrees.

In the embodiment, as illustrated in FIG. 7, preferably a rib 31R extending along the predetermined direction A from the upstream to the downstream is provided in an inner wall surface of the flavor source container 31. Although not particularly limited, preferably the number of ribs 31R is two or more. Preferably the downstream end portion of the ribs 31R does not reach the downstream end portion of the flavor source container 31. For example, in the predetermined direction A, a length L2 from the mesh body 32 to the downstream end portion of the ribs 31R is shorter than a length L1 from the mesh body 32 to the downstream end portion of the flavor source container 31. In other words, in a state in which the filter 33 is inserted in the flavor source container 31, preferably the downstream end portion of the ribs 31R contacts the filter 33 without reaching the downstream end portion of the flavor source container 31.

The mesh body 32 is provided on the upstream (non-mouthpiece side) than the flavor source 31A. In the embodiment, the mesh body 32 is provided on the upstream end portion of the flavor source container 31. When the mesh body 32 provided in the flavor source container 31 is very small, from the perspective of securing strength of the mesh body 32, preferably the flavor source container 31 and the mesh body 32 are integrally formed. That is, in the embodiment, the mesh body 32 is a part of the flavor source container 31. In such a case, preferably the flavor source container 31 and the mesh body 32 are configured by resin. For example, it is possible to use one or more resins that are selected from polypropylene, polyethylene terephthalate, polyethylene resin, and ABS resin as the resin. From the perspective of moldability and texture, preferably the resin is polypropylene. The flavor source container 31 and the mesh body 32 are constituted by metallic molding or injection molding.

In the embodiment, as illustrated in FIG. 8, the mesh body 32 has a plurality of openings 32A. Each of the plurality of openings 32A has a polygon shape that has an internal angle of 180° or less. Each of the plurality of openings 32A has, as widths through which each center of gravity of the plurality of openings 32A passes, a minimum width Wmin having the smallest width and a maximum width Wmax having the largest width. The minimum width Wmin is smaller than the lower limit of the size of the raw material pieces included in the flavor source 31A. More particularly, since the raw material pieces that actually constitutes the flavor source 31A are non-spherical, from the perspective of suppressing drop out of the raw material pieces, preferably the minimum width Wmin is smaller than ½ the lower limit of the size of the raw material pieces included in the flavor source 31A. The maximum width Wmax is larger than the minimum width Wmin. For example, preferably the maximum width Wmax is larger than the lower limit of the size of the raw material pieces. Alternatively, preferably the maximum width Wmax is from √2 times to six times of the minimum width Wmin. That is, each of the plurality of openings 32A is a shape different from a circle. Furthermore, since the raw material pieces tend not to fit in the opening 32A, preferably each of the plurality of openings 32A is a rectangular shape. Note that, each side of the rectangular shape that the opening 32A may include a nonlinear part generated in manufacturing the opening 32A. In addition, each vertex of the rectangular shape that the opening 32A may include a curved part generated in manufacturing the opening 32A.

Figure 9:
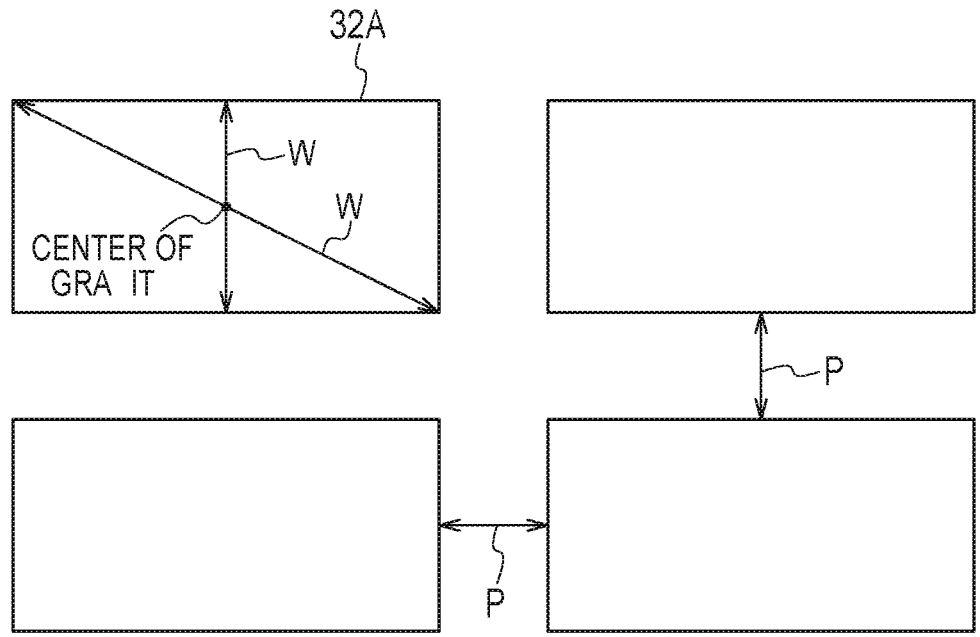
FIG. 9 is a diagram illustrating one example of a shape of an opening 32A according to the embodiment.
Figure 10:
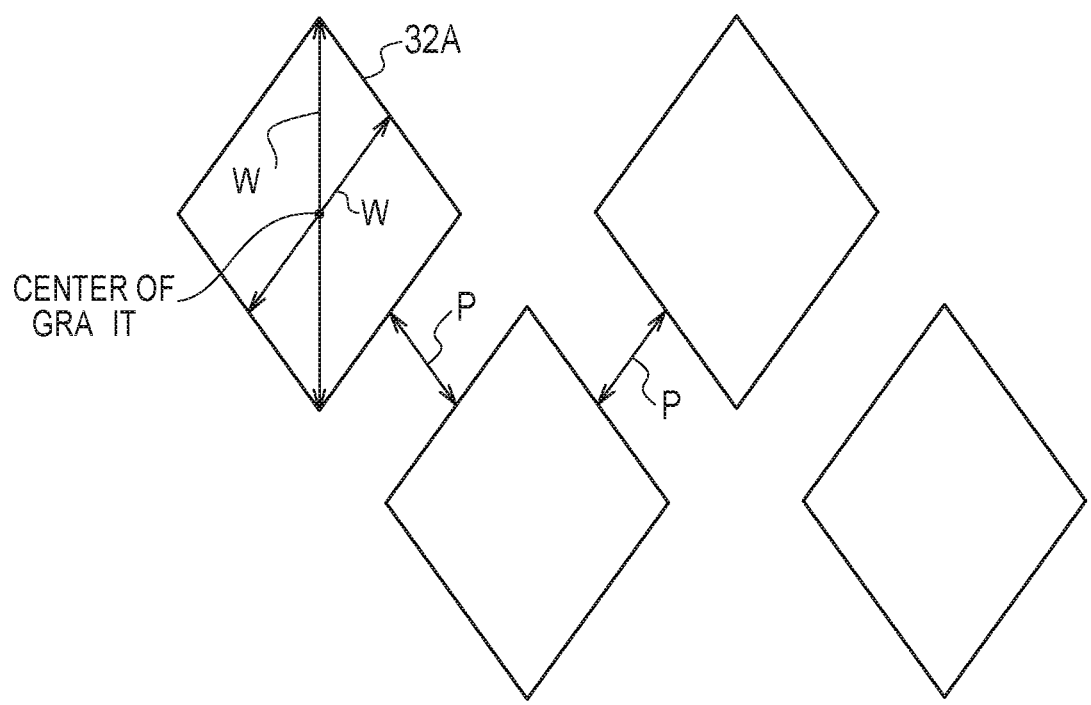
FIG. 10 is a diagram illustrating one example of the shape of the opening 32A according to the embodiment.
Figure 11:
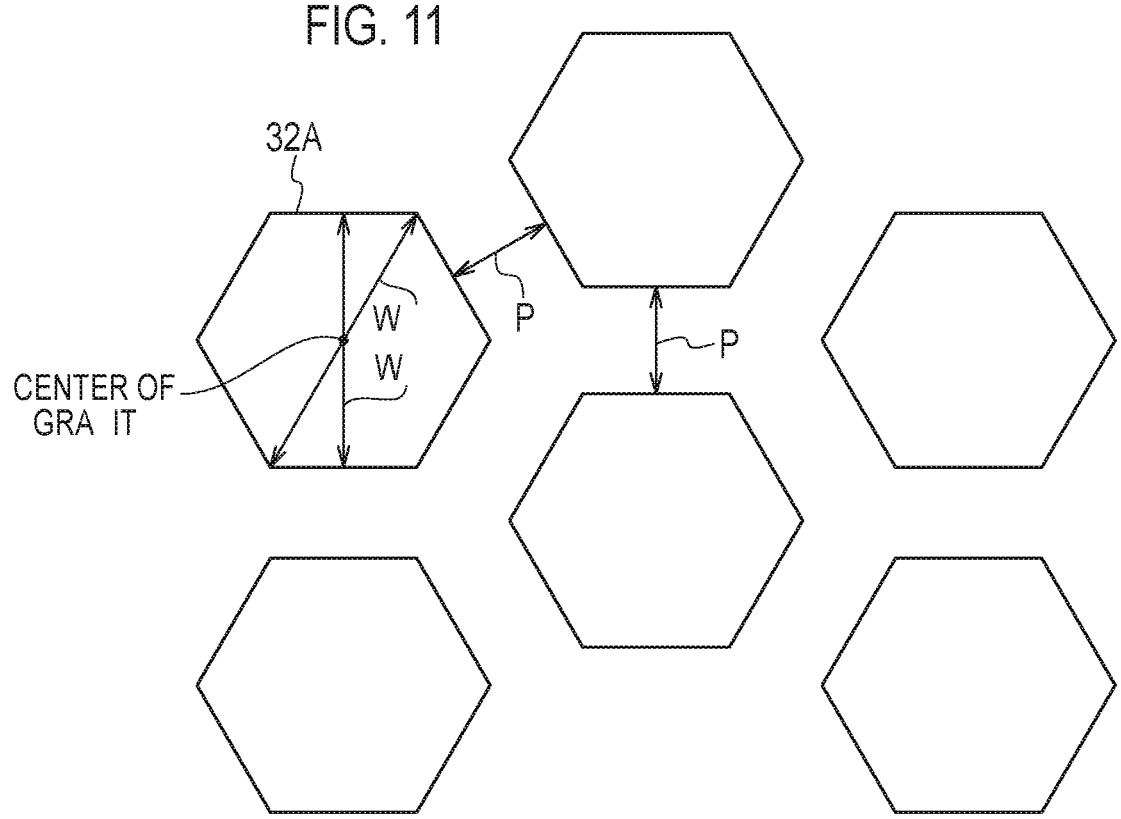
FIG. 11 is a diagram illustrating one example of the shape of the opening 32A according to the embodiment.
Figure 12:
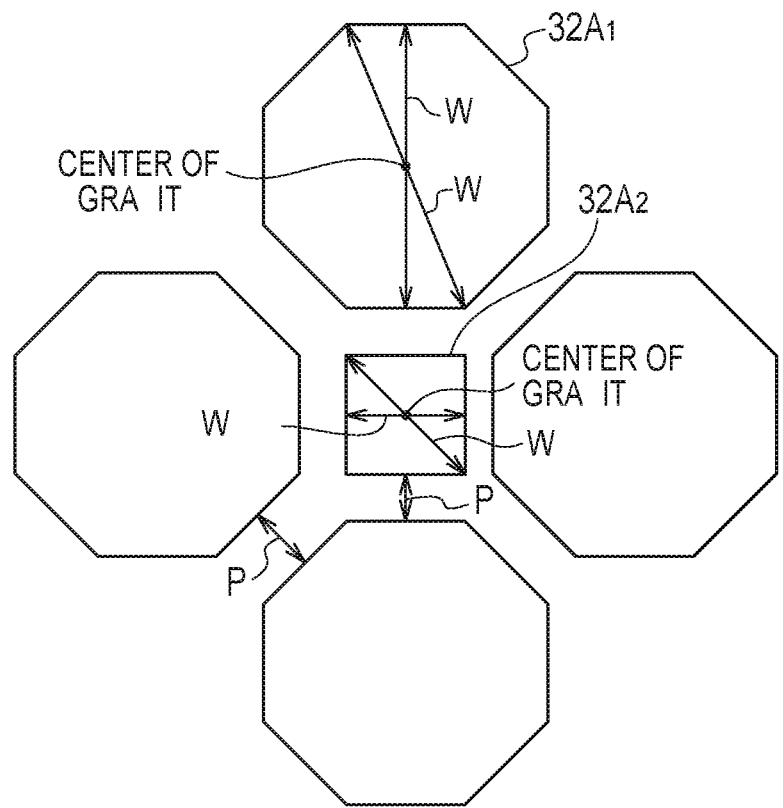
FIG. 12 is a diagram illustrating one example of the shape of the opening 32A according to the embodiment.

Here, as illustrated in FIG. 9 to FIG. 12, preferably each of the plurality of openings 32A has a shape selected from square, rectangular, diamond, hexagonal, and octagonal. As illustrated in FIG. 9 to FIG. 11, the shape of each of the plurality of openings 32A may be one type, and as illustrated in FIG. 12, may be two types. The shape of each of the plurality of openings 32A may be three types or more. Note that, from the perspective of arrangement efficiency, manufacturability, or the like of the plurality of openings 32A, preferably each of the plurality of openings 32A has a rectangular shape.

In the examples illustrated in FIG. 9 to FIG. 12, preferably the plurality of openings 32A are provided such that sides of the openings 32A adjacent to each other become parallel. Preferably an interval P of the openings 32A adjacent to each other is from 0.15 to 0.30 mm. In such a case, preferably the thickness of the mesh body 32 is from 0.1 to 1 mm.

The filter 33 is configured by a predetermined fiber and has a roughness to a degree such that the raw material pieces do not pass through. The filter 33 is provided on the downstream than the flavor source 31A. For example, the filter 33 is an acetate filter. The cap 34 is provided on the downstream (on the mouthpiece side) than the filter 33.

Note that, preferably the flavor source container 31 (here, containing the mesh body 32), the filter 33, and the cap 34 are adhered or welded to each other.

In the embodiment, preferably all openings provided in the mesh body 32 are the opening 32A described above, but the embodiment is not limited to this. The openings provided in the mesh body 32 may include openings other than the opening 32A described above.

(Connection State)

Figure 13:
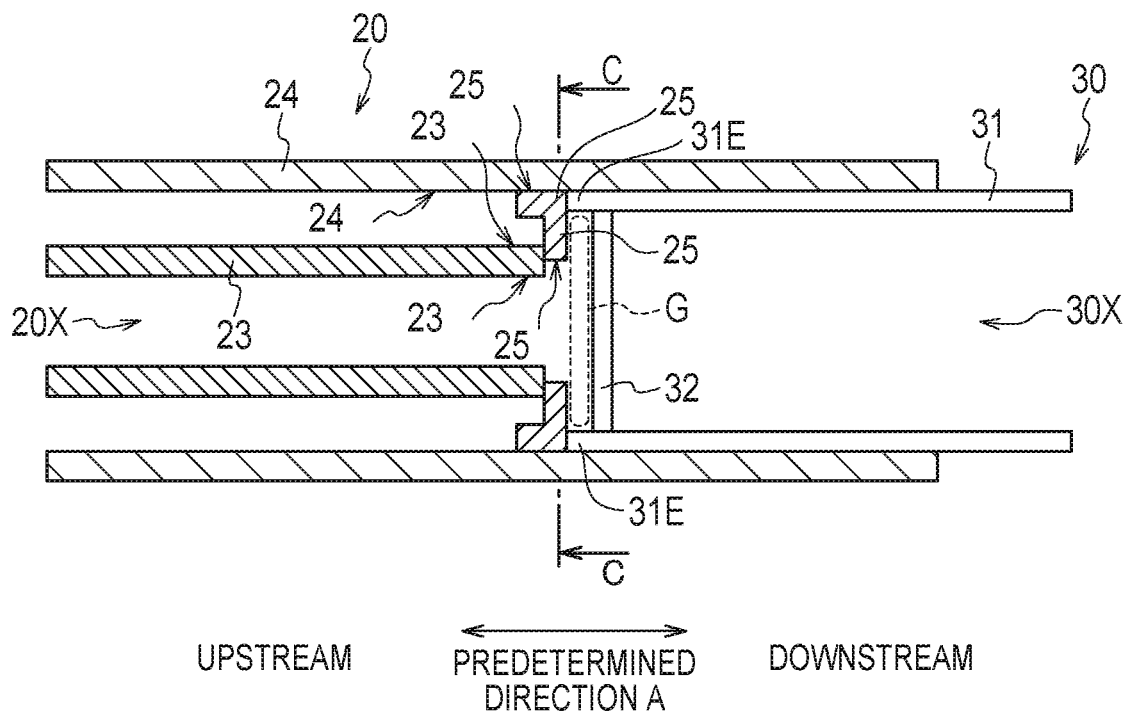
FIG. 13 is a diagram illustrating a connection state of the first cartridge 20 and the second cartridge 30 according to the embodiment.
Figure 14:
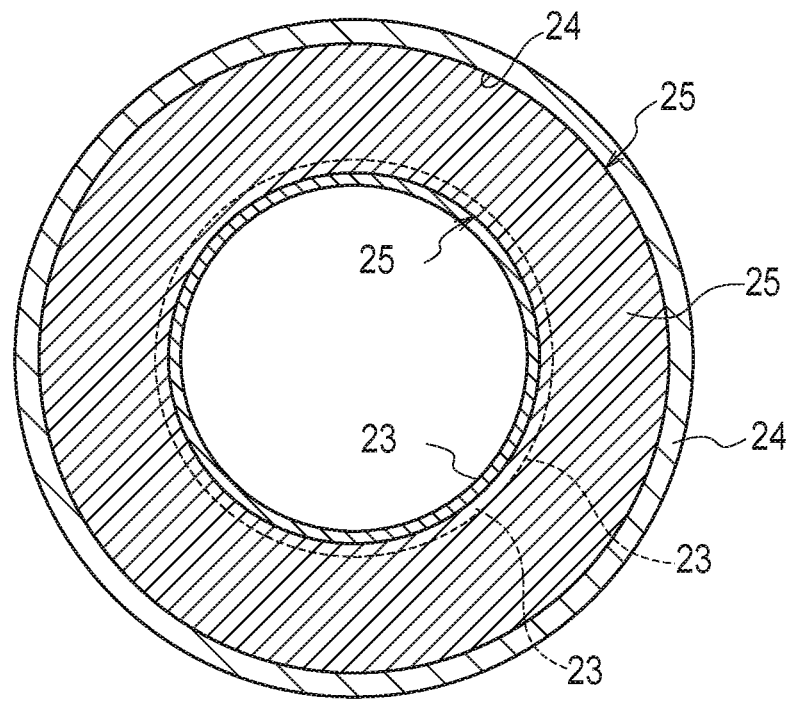
FIG. 14 is a diagram illustrating the cross section taken along C-C illustrated in FIG. 13.

Hereinafter, a connection state of the first cartridge 20 and the second cartridge 30 according to the embodiment will be described. FIG. 13 is a diagram illustrating a connection state of the first cartridge 20 and the second cartridge 30 according to the embodiment. FIG. 14 is a diagram illustrating the cross-section taken along C-C illustrated in FIG. 13. However, it should be noted that in FIG. 13, the reservoir 21, the atomizer 22, the flavor source 31A, the filter 33, and the cap 34 are omitted.

As illustrated in FIG. 13, an aerosol flow adjustment chamber G that adjusts the flow of aerosol supplied from the first flow path 20X is provided between the first flow path 20X and the second flow path 30X such that polarization of the flow of the aerosol in the second flow path 30X is suppressed. In the embodiment, the aerosol flow adjustment chamber G is formed between the downstream end portion of the flow path forming body 23 and the upstream end portion of the flavor source container 31. More particularly, the aerosol flow adjustment chamber G is formed between the end cap 25 and the mesh body 32.

Here, a filling rate of the flavor source 31A accommodated in the flavor source container 31 may not be 100% of the capacity of the flavor source container 31. That is, a gap may be formed in the flavor source container 31. However, it is needless to say that the aerosol flow adjustment chamber G has a different gap generated by the filling rate of the flavor source 31A not being 100%.

In the embodiment, in a cross section orthogonal to the predetermined direction A, a shifted distance may be defined by a distance from an outer edge of the first flow path 20X to an outer surface of the second flow path 30X on a line from the center of gravity of the first flow path 20X toward the outside of the first flow path 20X. A length LG of the aerosol flow adjustment chamber G in the predetermined direction A may be determined based on the largest shift distance among the shift distances. That is, the length LG of the aerosol flow adjustment chamber G may be determined according to the largest shift distance. From the perspective of suppressing polarization of flow of the aerosol that flows inside the flavor source container 31, preferably the longer the largest shift distance, the longer the length LG of the aerosol flow adjustment chamber G. Preferably the length LG of the aerosol flow adjustment chamber G is 1/10 or more of the largest shift distance.

For example, as illustrated in FIG. 14, in the cross section orthogonal to the predetermined direction A, when the first flow path 20X and the second flow path 30X are coaxial circles, the length LG of the aerosol flow adjustment chamber G in the predetermined direction A is determined according to a difference (that is, the shift distance) between a radius R1 of the first flow path 20X and a radius R2 of the second flow path 30X.

In the embodiment, as described above, the flavor source container 31 has a protruding portion 31E that protrudes to the upstream side (in the embodiment, the flow path forming body 23 or the end cap 25 side) from an outer edge of an upstream end portion (here, the mesh body 32) of the flavor source container 31 in a cross section orthogonal to the aerosol flow path (predetermined direction A). That is, the flavor source container 31 has the protruding portion 31E (first protruding portion) as a spacer that forms the aerosol flow adjustment chamber G.

In the embodiment, preferably the entirety of the downstream end portion of the flow path forming body 23 (first flow path 20X) is exposed to the aerosol flow adjustment chamber G. Preferably the entirety of the upstream end portion of the flavor source container 31 (second flow path 30X) is exposed to the aerosol flow adjustment chamber G. Thereby, it is possible to effectively adjust the flow of the aerosol led from the first flow path 20X to the second flow path 30X using the aerosol flow adjustment chamber G.

Preferably the aerosol flow adjustment chamber G does not contain a part that protrudes more to the upstream side than the downstream end portion of the flow path forming body 23 (first flow path 20X). Preferably the aerosol flow adjustment chamber G does not contain a part that protrudes more to the downstream side than the upstream end portion of the flavor source container 31 (second flow path 30X). Thereby, it is possible to suppress retention of aerosol in an unnecessary gap.

Preferably an inner wall surface that constitutes the aerosol flow adjustment chamber G is continuous without including a step from the outer edge of the downstream end portion of the flow path forming body 23 (first flow path 20X) across the outer edge of the upstream end portion of the flavor source container 31 (second flow path 30X).

In the embodiment, as illustrated in FIG. 13 and FIG. 14, in the cross section orthogonal to the aerosol flow path (predetermined direction A), preferably an outer edge 25out of the end cap 25 contacts an inner wall surface 24in of an outer frame 24 and an inner edge 25in of the end cap 25 is positioned between the outer edge 23out of the flow path forming body 23 and the inner edge 23in of the flow path forming body 23. Thereby, it is difficult to remove the end cap 25 from the downstream side. In addition, when the end cap 25 is provided inside the outer frame 24, it is difficult for the end cap 25 to interfere with the flow path forming body 23.

(Control Circuit)

Figure 15:
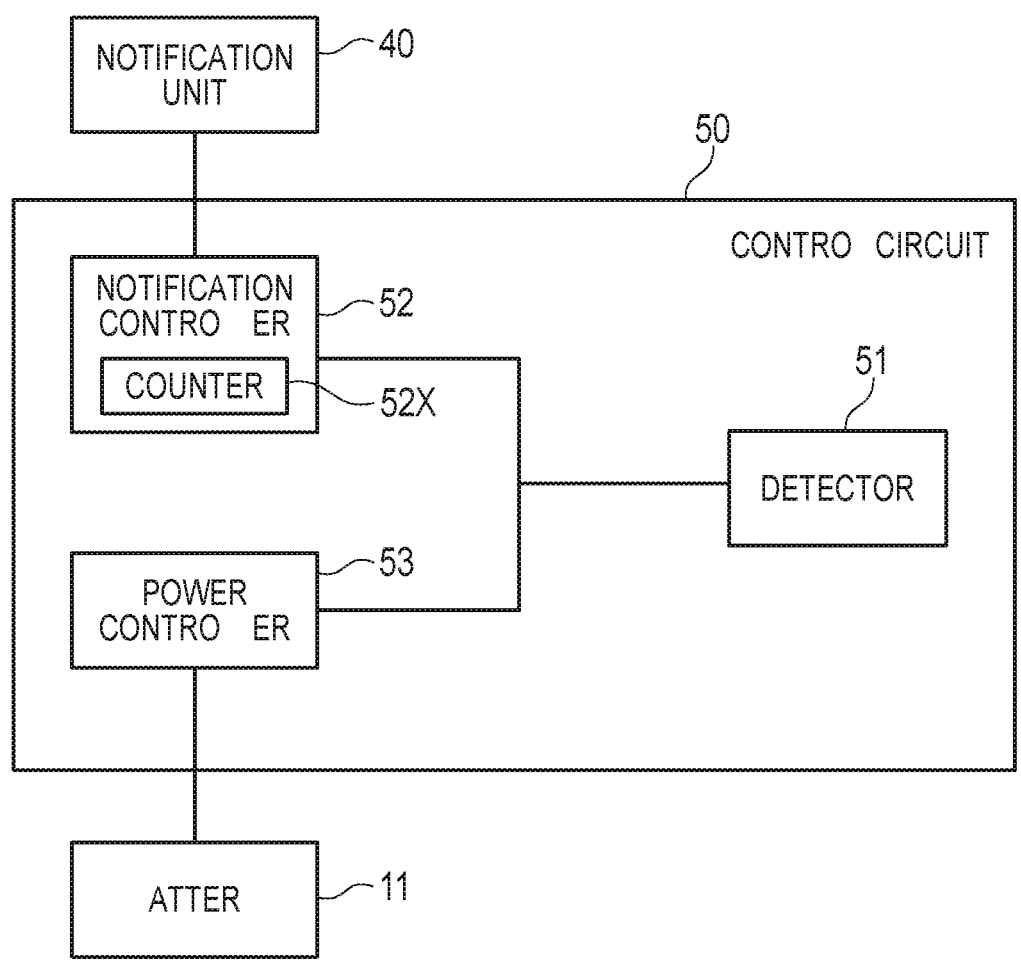
FIG. 15 is a diagram mainly illustrating a function block of a control circuit 50 according to the embodiment.

A control circuit according to the embodiment will be mainly described below. FIG. 15 is a diagram mainly illustrating a function block of a control circuit 50 according to an embodiment.

As illustrated in FIG. 15, the non-burning type flavor inhaler 1 has a notification unit 40 and the control circuit 50.

The notification unit 40 notifies a variety of information. The notification unit 40 may be constituted by a light emitting element, may be constituted by a vibration element, and may be constituted by a sound output element. The notification unit 40 may combine two or more elements out of the light emitting element, the vibration element, and the sound output element. Preferably the notification unit 40 is provided in the power source unit 10, but the embodiment is not limited thereto. The notification unit 40 may be provided in the first cartridge 20 and may be provided in the second cartridge 30.

The control circuit 50 has a detector 51, a notification controller 52, and a power controller 53.

The detector 51 detects the puff action. In such a case, the detector 51 is connected to an inhalation sensor and detects the puff action based on an output result of the inhalation sensor. In addition, the detector 51 detects power supply from the battery 11 to the atomizer 22. In such a case, the detector 51 is connected to a voltage sensor provided on a power line that connects the battery 11 and the atomizer 22 and detects power supply based on the output result of the voltage sensor.

The notification controller 52 controls the notification unit 40 to notify various information. For example, the notification controller 52 controls the notification unit 40 to notify a replacement timing of the second cartridge 30 according to detection of the replacement timing of the second cartridge 30. As described above, the notification unit 40 may notify the replacement timing of the second cartridge 30 due to light emission by the light emitting element, may notify the replacement timing of the second cartridge 30 due to vibration by the vibration element, and may notify the replacement timing of the second cartridge 30 due to sound output by the sound output element.

Here, the notification controller 52 detects the replacement timing of the second cartridge 30 based on the number of puff actions or an energization time of the atomizer 22. Note that, the number of puff actions may be set according to the puff action detected by the detector 51 described above. In the same manner, the energization time of the atomizer 22 may be set according to the power supply detected by the detector 51 described above.

Specifically, the notification controller 52 has a counter 52X that counts the number of puff actions or the energization time of the atomizer 22. When a count value of the counter 52X reaches a predetermined value, the notification controller 52 detects the replacement timing of the second cartridge 30 and resets the count value of the counter 52X. Note that, preferably the notification controller 52 resets the count value of the counter 52X after the second cartridge 30 is replaced. Alternatively, when the count value of the counter 52X reaches the predetermined value, the notification controller 52 notifies the replacement timing of the second cartridge 30 and resets the count value of the counter 52X according to the predetermined operation of the user. when a hardware interface (for example, a switch or button) for switching the power source of the non-burning type flavor inhaler 1 on or off or a hardware interface (for example, a switch or a button) for controlling power supply to the atomizer 22 is provided in the non-burning type flavor inhaler 1, the predetermined operation of the user may be an operation of the hardware interface. Alternatively, the predetermined user operation may be an operation of taking in breath from the mouthpiece of the non-burning type flavor inhaler 1 if it is possible for the detector 51 to detect the puff action. Alternatively, the predetermined operation of the user may be an operation of inhaling breath (for example, an operation of inhaling two times in a short time) in a mode in which it is possible for the detector 51 to detect the puff action and it is possible to identify a general puff action. The counter 52X may be a count type counter and may be a countdown type counter.

In the embodiment, preferably the notification controller 52 controls the notification unit 40 to notify the replacement timing of the first cartridge 20 according to detection of the replacement timing of the first cartridge 20. In such a case, preferably the notification controller 52 detects the replacement timing of the first cartridge 20 based on the number of replacement times of the second cartridge 30. More particularly, the notification controller 52 detects the replacement timing of the first cartridge 20 when the number of replacement times of the second cartridge 30 reaches a predetermined number of times.

In the embodiment, preferably the notification controller 52 controls the notification unit 40 to notify the replacement timing of the battery 11 or the charging timing of the battery 11 according to detection of the replacement timing of the battery 11 or the charging timing of the battery 11. In such a case, preferably the notification controller 52 detects the replacement timing of the battery 11 or the charging timing of the battery 11 based on output voltage of the battery 11. More particularly, preferably the notification controller 52 detects the replacement timing or the charging timing of the battery 11 when the output voltage of the battery 11 is a predetermined threshold.

However, the embodiment is not limited thereto, but the notification controller 52 may detect the replacement timing of the battery 11 or the charging timing of the battery 11 based on the number of puff actions or the energization time of the atomizer 22. More particularly, the notification controller 52 may detect the replacement timing of the battery 11 or the charging timing of the battery 11 when the number of puff actions or the energization time of the atomizer 22 exceeds the predetermined threshold.

Note that, the notification unit 40 notifies the replacement timing of the first cartridge 20, the replacement timing of the battery 11, or the charging timing of the battery 11 according to the light emission of the light emitting element, the vibration of the vibration element, or the output sound of the sound output element in the same manner as the replacement timing of the second cartridge 30.

The power controller 53 outputs a predetermined instruction to the battery 11 as an instruction to the battery 11, the predetermined instruction instructing the battery 11 to make the aerosol amount, atomized by the atomizer 22, falls within the desired range. The output of the predetermined instruction may be performed one time in each puff action. In addition, it should be noted that the power controller 53 instructs output of power to the atomizer 22 to the battery 11 in the puff period in which the puff action is performed, but does not instruct output of power to the atomizer 22 to the battery 11 in the non-puff period in which the puff action is not performed. Note that, the puff period and the non-puff period may be set according to the puff action detected by the detector 51 described above.

Here, the power controller 53 controls the predetermined instruction such that the aerosol amount atomized by the atomizer 22 falls within the desired range. For example, the power controller 53 modifies the predetermined instruction accompanying a reduction of the accumulated amount in the battery 11. In addition, the power controller 53 stops power supply from the battery 11 to the atomizer 22 when the predetermined period elapses from the start of power supply to the atomizer 22. In other words, the power controller 53 stops power supply from the battery 11 to the atomizer 22 when the puff period exceeds the predetermined period even in the puff period in which the puff action is actually performed by the user.

In addition, the power controller 53 stops power supply from the battery 11 to the atomizer 22 when the puff action ends even prior to the predetermined period elapse from the start of the puff action. Thereby, since the aerosol is not generated in the period in which the puff action is not performed (non-puff period), it is possible to suppress a situation in which droplets are generated by retaining and condensing the aerosol in the aerosol flow path in the non-puff period and the aerosol generated by the puff action next to the non-puff period is trapped in the droplets, and suppress a concern of hindering supply of the aerosol amount in the desired range, deterioration of taste caused by the droplets, and the like.

Here, the predetermined period is shorter than the upper limit value of the standard puff period derived from statistics of the puff period of the user. Furthermore, preferably the predetermined period is shorter than an average value of the puff period derived from statistics of the puff period of the user. Of course, the average value of the puff period is shorter than the upper limit value of the standard puff period.

Since the predetermined period is determined to suppress variation of the puff period of the user, it is necessary for there to be a certain number or more of users whose puff period is longer than the predetermined period. From such a perspective, preferably the predetermined period is derived from statistics. Furthermore, since it is possible for the energization time of the atomizer 22 in most puff actions is fixed in the predetermined period by the predetermined period being shorter than the average value of the puff period derived from statistics, it is possible to suppress variation of the aerosol amount caused by variance of the puff period of the user.

For example, the predetermined period is from one to three seconds. By the predetermined period being one second or more, the energization time of the atomizer 22 is not too short compared to the puff period, and therefore discomfort imparted to the user is mitigated. Meanwhile, it is possible to set the puff action in which the energization time of the atomizer 22 is fixed to the predetermined period to a certain number or more by the predetermined period being three seconds or less.

Furthermore, the predetermined period may be from 1.5 to 2.5 seconds. Thereby, it is possible to mitigate discomfort imparted to the user, and increase the puff action in which the energization time of the atomizer 22 is fixed to the predetermined period.

In the embodiment, preferably the predetermined period is set in advance. In such a case, preferably the predetermined period is determined according to the standard puff period derived from statistics of puff periods of a plurality of users.

Note that, the standard puff period may be derived from statistics of puff periods of users, and is a period between the lower limit value of puff periods of a plurality of users and the upper limit value of puff periods of a plurality of users. The lower limit value and the upper limit value, for example, may be derived from the upper limit value and the lower limit value of a 95% confidence interval of the average value and may be derived as m±nσ (here, m is the average value, σ is standard deviation, and n is a positive real number) based on distribution of puff period data of the users.

In the embodiment, preferably the power controller 53 modifies (or corrects) the predetermined instruction such that the aerosol amount atomized by the atomizer 22 falls within the desired range accompanying the reduction of the accumulated amount in the battery 11. For example, when the amount of power supplied from the battery 11 to the atomizer 22 is controlled by pulse control, preferably the power controller 53 increases a duty ratio output to the battery 11 in one puff action accompanying the reduction of the accumulated amount in the battery 11 as a modification of the predetermined instruction.

Figure 16:
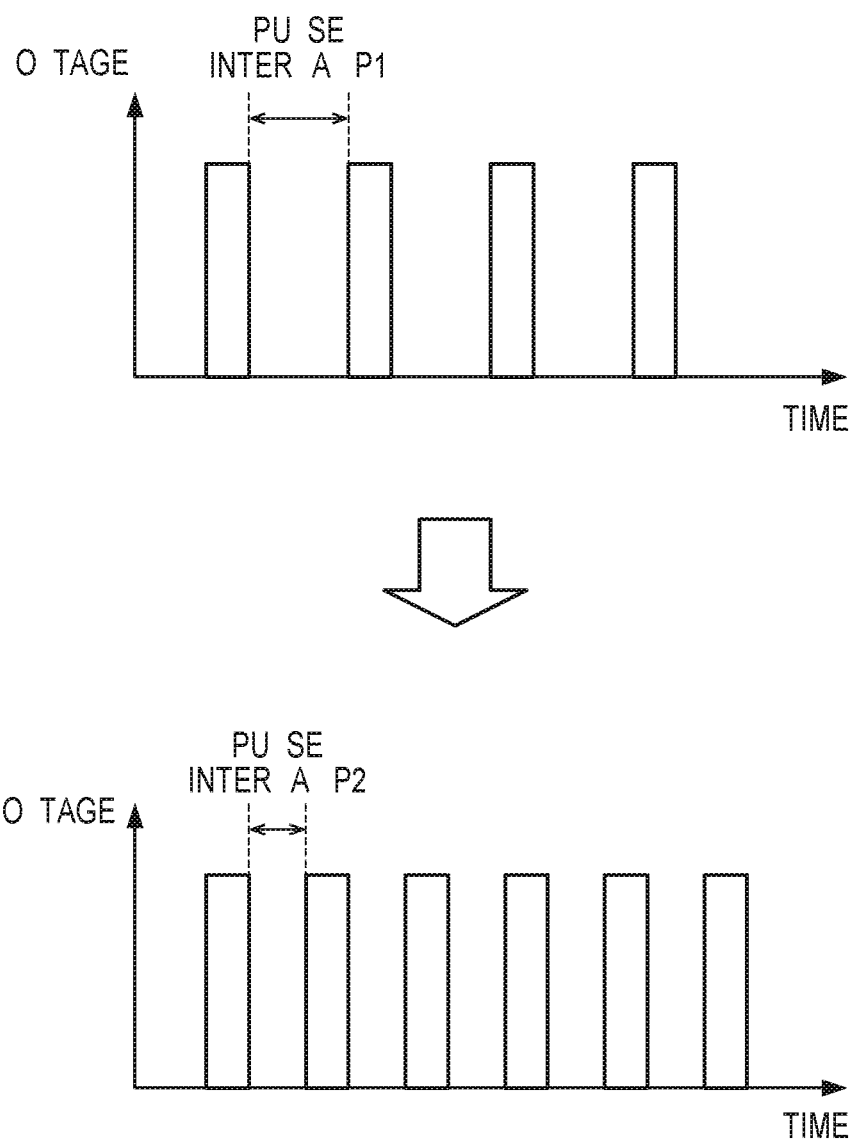
FIG. 16 is a diagram illustrating one example of duty ratio control according to the embodiment.

As illustrated in FIG. 16, for example, the power controller 53 controls an interval (pulse interval) of an on time at which power is supplied from the battery 11 to the atomizer 22. Specifically, the power controller 53 increases the duty ratio output to the battery 11 in one puff action by modifying a pulse interval P1 to a pulse interval P2.

Figure 17:
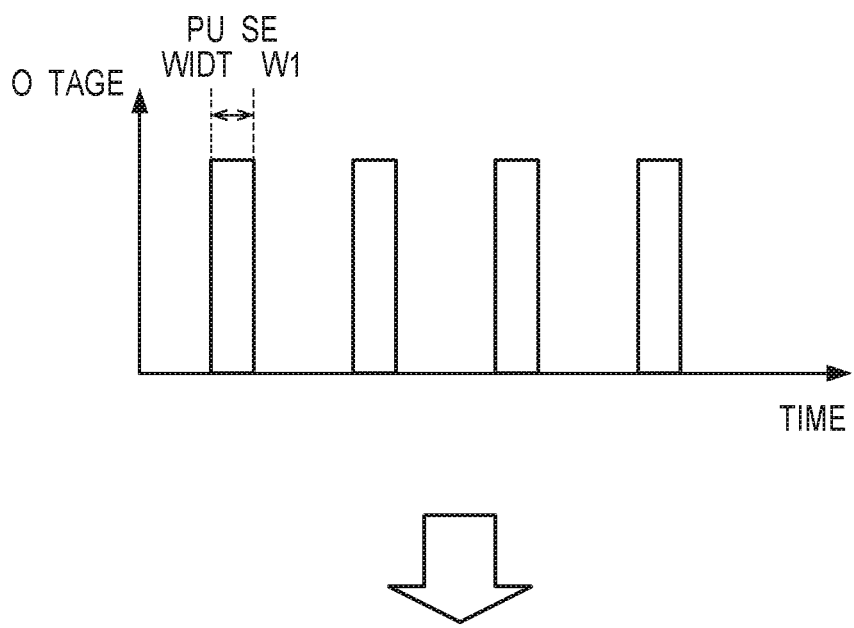
FIG. 17 is a diagram illustrating one example of duty ratio control according to the embodiment.
Figure 17:
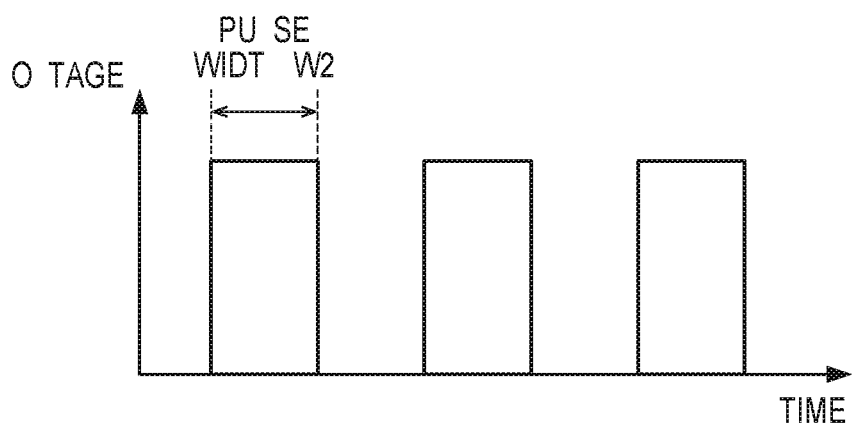

Alternatively, as illustrated in FIG. 17, the power controller 53 controls a length (pulse width) of the on time at which power is supplied from the battery 11 to the atomizer 22. Specifically, the power controller 53 increases the duty ratio output to the battery 11 in one puff action by modifying a pulse width W1 to a pulse width W2.

Note that, the power controller 53 may gradually increase the duty ratio and may continuously increase the duty ratio as a modification of the predetermined instruction accompanying the reduction of the accumulated amount in the battery 11.

In the embodiment, preferably the power controller 53 estimates the accumulated amount in the battery 11 based on a voltage value output from the battery 11. Alternatively, the power controller 53 may estimate the accumulated amount in the battery 11 based on the number of times of the puff action and the energization time of the atomizer 22. Note that, the number of puff actions may be set according to the puff action detected by the detector 51 described above. In the same manner, the energization time of the atomizer 22 may be set according to the power supply detected by the detector 51 described above.

In the embodiment, preferably the power controller 53 stops the power supply from the battery 11 to the atomizer 22 from the count value of the counter 52X reaching the predetermined value until the count value is reset. In other words, preferably the power controller 53 stops the power supply from the battery 11 to the atomizer 22 from the notification of the replacement timing of the second cartridge 30 until the count value is reset. That is, power supply from the battery 11 to the atomizer 22 is stopped until the second cartridge 30 is replaced. Accordingly, use of the second cartridge 30, in which it is only possible to impart a small amount of flavor to the aerosol, is suppressed.

(Control Method)

Figure 18:
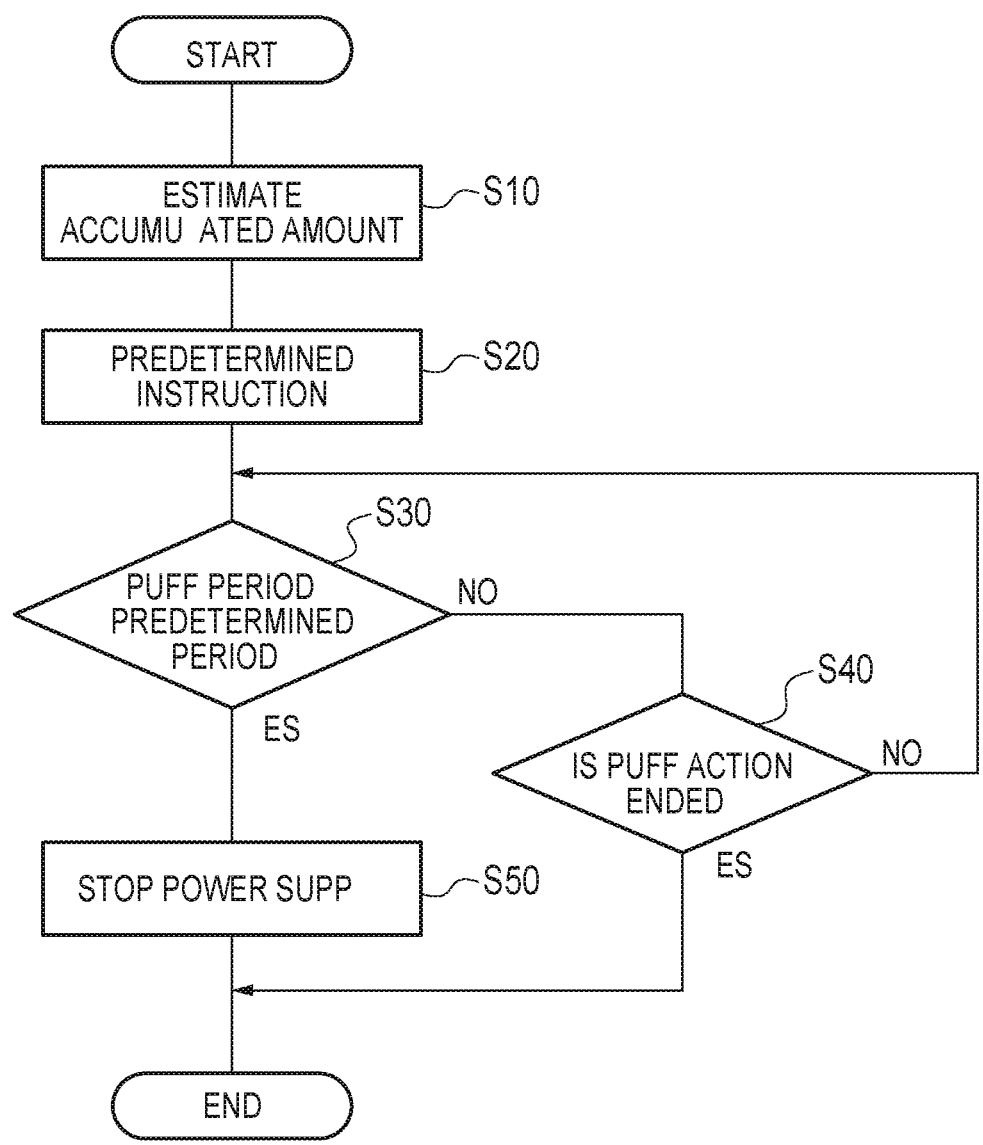
FIG. 18 is a flowchart illustrating a control method according to the embodiment.

A control method according to the embodiment will be described below. FIG. 18 is a flowchart illustrating the control method according to the embodiment. FIG. 18 is a flowchart illustrating the control method of the amount of power supplied from the battery 11 to the atomizer 22 in one puff action. It is noted that the flow illustrated in FIG. 18 starts in response to detection of the start of the puff action.

It is noted that as the premise of the flow illustrated in FIG. 18, the non-burning type flavor inhaler 1 (that is, the power controller 53) instructs to the battery 11 output of power to the atomizer 22 in the puff period in which the puff action is performed, but does not instruct to the battery 11 output of power to the atomizer 22 in the non-puff period in which the puff action is not performed.

As illustrated in FIG. 18, in step S10, the non-burning type flavor inhaler 1 (that is, the power controller 53) estimates the accumulated amount in the battery 11. As described above, preferably the non-burning type flavor inhaler 1 estimates the accumulated amount in the battery 11 based on the voltage value output from the battery 11.

In step S20, the non-burning type flavor inhaler 1 (that is, the power controller 53) determines the predetermined instruction (for example, the duty value) output to the battery 11. More particularly, the non-burning type flavor inhaler 1 determines the duty ratio output to the battery 11 such that the duty ratio increases along with the reduction of the accumulated amount in the battery 11. In other words, the non-burning type flavor inhaler 1 increases the duty ratio as a modification of the predetermined instruction.

In step S30, the non-burning type flavor inhaler 1 (that is, the power controller 53) determines whether or not the predetermined period elapses from the start of power supply to the atomizer 22. In other words, the non-burning type flavor inhaler 1 determines whether or not the puff period exceeds the predetermined period. When the determination result is YES, the non-burning type flavor inhaler 1 transitions to a process in step S50, and when the determination result is NO, the non-burning type flavor inhaler 1 transitions to a process in step S40.

In step S40, the non-burning type flavor inhaler 1 (that is, the power controller 53) estimates whether or not the puff action ends. When the determination result is NO, the non-burning type flavor inhaler 1 returns to the process in step S30, and when the determination result is YES, the non-burning type flavor inhaler 1 stops power supply to the atomizer 22 and ends the series of processes. Note that, as described above, the end of the puff action may be detected by the detector 51 if it is possible for the detector 51 to detect the puff action. Alternatively, the end of the puff action may be detected according to the operation of the hardware interface (for example, the switch or the button) for switching whether or not power is supplied to the atomizer 22.

In step S50, the non-burning type flavor inhaler 1 (that is, the power controller 53) stops power supply from the battery 11 to the atomizer 22 even in the puff period in which the puff action is actually performed by the user.

(Operation and Effect)

In the embodiment, the power controller 53 stops power supply from the battery 11 to the atomizer 22 when the predetermined period elapses from starting power supply to the atomizer 22. The predetermined period is shorter than the upper limit value of the standard puff period derived from statistics of puff periods of users. Accordingly, even if the non-burning type flavor inhaler is used by the user who has a puff period longer than the predetermined period, it is easy to suppress an extreme decrease of the accumulated amount in the battery 11 and easy to control the predetermined instruction such that the aerosol amount atomized by the atomizer 22 falls within the desired range.

In this manner, it is possible that the aerosol amount supplied per one puff action falls within the desired range through the puff action from the start of smoking (an initial stage in which an accumulated amount in a battery 11 is sufficient) until the end of smoking (that is, a final stage in which the accumulated amount in the battery 11 decreases), regardless of the length of a puff period of the user and the accumulated amount in the battery 11.

In the embodiment, the power controller 53 modifies the predetermined instruction output to the battery 11 in one puff action accompanying the reduction of the accumulated amount in the battery 11. It is possible to suppress a difference in the amount of power actually supplied from the battery 11 to the atomizer 22 between an initial step in which the accumulated amount in the battery 11 is sufficient and a final stage in which the accumulated amount in the battery 11 is insufficient. Thereby, it is possible for the aerosol amount atomized by the atomizer 22 to fall in the desired range regardless of the length of the puff period of the user and the accumulated amount in the battery 11.

In the embodiment, the notification controller 52 controls the notification unit 40 to notify a replacement timing of the second cartridge 30 according to detection of the replacement timing of the second cartridge 30. Accordingly, it is possible for the user to easily ascertain the replacement timing of the second cartridge 30.

In the embodiment, the notification controller 52 controls the notification unit 40 to notify the replacement timing of the first cartridge 20 according to detection of the replacement timing of the first cartridge 20. Accordingly, it is possible for the user to easily ascertain the replacement timing of the first cartridge 20.

In the embodiment, the notification controller 52 detects the replacement timing (lifespan) of the first cartridge 20 based on the number of replacement times of the second cartridge 30. Accordingly, detection of the replacement timing of the first cartridge 20 is easy. Furthermore, it is possible to mitigate a possibility that the lifespan of the first cartridge 20 comes to an end while the second cartridge 30 is in use. Note that, of course the replacement timing (lifespan) of the first cartridge 20 corresponds to the number (number of times of replacement) of the second cartridge 30 usable in one first cartridge 20.

In the embodiment, the notification controller 52 controls the notification unit 40 to notify the replacement timing of the battery 11 or the charging timing of the battery 11 according to detection of the replacement timing of the battery 11 or the charging timing of the battery 11. Accordingly, it is possible for the user to easily ascertain the replacement timing of the battery 11 or the charging timing of the battery 11.

In the embodiment, the power controller 53 stops the power supply from the battery 11 to the atomizer 22 from the count value of the counter 52X reaching the predetermined value until the count value is reset. Accordingly, power supply from the battery 11 to the atomizer 22 is stopped until the second cartridge 30 is replaced. Accordingly, use of the second cartridge 30, in which it is only possible to impart a small amount of flavor to the aerosol, is suppressed.

In the embodiment, the power controller 53 stops power supply from the battery 11 to the atomizer 22 when the predetermined instruction is controlled such that the aerosol amount atomized by the atomizer 22 falls within the desired range and a predetermined period elapses from the start of power supply to the atomizer 22. Accordingly, since the variation of the amount of power consumed in one puff action reduces, the detection accuracy of the replacement timing of the second cartridge 30 is improved when the replacement timing of the second cartridge 30 is detected based on the number of puff actions.

In the embodiment, an aerosol flow adjustment chamber G that adjusts the flow of aerosol supplied from the first flow path 20X is provided between the first flow path 20X and the second flow path 30X such that polarization of the flow of the aerosol in the second flow path 30X is suppressed. Thereby, the flavor source tends to pass through without the aerosol supplied from the first flow path 20X biasing in the second cartridge 30X.

In the embodiment, the reservoir 21 is positioned on the periphery of the flow path forming body 23 in a cross section orthogonal to the first flow path 20X (predetermined direction A). Thereby, it is possible to secure the volume of the reservoir 21 in which the aerosol source 21A is retained while suppressing the entire length of the first cartridge 20 in the first flow path 20X (predetermined direction A).

In the embodiment, in the cross section orthogonal to the aerosol flow path (predetermined direction A), the size of the second flow path 30X is larger than the size of the first flow path 20X. In other words, since the first flow path 20X is small in the cross section orthogonal to the aerosol flow path (predetermined direction A), it is possible to secure volume of the reservoir 21 positioned on the periphery of the flow path forming body 23. Since the size of the second flow path 30X is large in the cross section orthogonal to the aerosol flow path (predetermined direction A), it is possible to efficiently remove the flavor component from the flavor source 31A.

In the embodiment, in the cross section orthogonal to the aerosol flow path (predetermined direction A), the outer edge 25out of the end cap 25 contacts the inner wall surface 24in of the outer frame 24 and the inner edge 25in of the end cap 25 is positioned between the outer edge 23out of the flow path forming body 23 and the inner edge 23in of the flow path forming body 23. Thereby, it is difficult to remove the end cap 25 from the downstream side. In addition, when the end cap 25 is provided inside the outer frame 24, it is difficult for the end cap 25 to interfere with the flow path forming body 23.

In the embodiment, in a cross section orthogonal to the predetermined direction A, when a distance from an outer edge of the first flow path 20X to an outer surface of the second flow path 30X is a shifted distance on a line from the center of gravity of the first flow path 20X toward the outside of the first flow path 20X, a length LG of the aerosol flow adjustment chamber G in the predetermined direction A is determined according to the largest shift distance. Thereby, it is possible to appropriately adjust the flow of the aerosol led from the first 20X to the second flow path 30X using the aerosol flow adjustment chamber G, and the flavor source 31A tends to pass through without the aerosol supplied from the first flow path 20X biasing in the second cartridge 30.

In the embodiment, each of the plurality of openings 32A provided in the mesh body 32 has a polygon shape that has an internal angle of 180° or less. Each of the plurality of openings 32A has a minimum width Wmin having the smallest width and a maximum width Wmax having the largest width as widths through which each center of gravity of the plurality of openings 32A passes. Here, since the minimum width Wmin is smaller than the size of the raw material pieces included in the flavor source 31A, it is possible to suppress drop out of the raw material pieces included in the flavor source 31A, and since the maximum width Wmax is larger than the minimum width Wmin, it is possible to increase an opening ratio for the entirety of the mesh body.

In this manner, it is possible to secure the opening ratio for the entirety of the mesh body 32 while suppressing drop out of the raw material pieces forming the flavor source in the second cartridge 30 for the non-burning type flavor inhaler.

In the embodiment, the maximum width Wmax of the opening 32A is larger than the lower limit of the size of the raw material pieces included in the flavor source 31A. Accordingly, the opening ratio is improved for the entirety of the mesh body 32.

In the embodiment, the maximum width Wmax of the opening 32A is from $\sqrt{2}$ times to six times of the minimum width Wmin of the opening 32A. Accordingly, it is possible to improve the opening ratio for the entirety of the mesh body 32 by the maximum width Wmax being $\sqrt{2}$ times or more of the minimum width Wmin and maintain the strength of the mesh body 32 by the maximum width Wmax being six times or less of the minimum width Wmin.

In the embodiment, each of the plurality of openings 32A has a shape selected from square, rectangular, diamond, hexagonal, and octagonal. The plurality of openings 32A are provided such that sides of the openings 32A adjacent to each other become parallel. The interval P of the openings 32A that are adjacent to each other are from 0.15 to 0.30 mm. Thereby, it is possible to efficiently provide the plurality of openings 32A, and it is possible to maintain the strength of the mesh body 32 while improving the opening ratio for the entirety of the mesh body 32.

In the embodiment, the inner wall surface of the flavor source container 31 is provided with the rib 31R extending along the predetermined direction A from the upstream to the downstream. Accordingly, the flavor component tends to be removed from the flavor source 31A without the flow of the aerosol in the predetermined direction A being inhibited by the rib 31R in the flavor source container 31 while the rib 31R reinforces the flavor source container 31.

In the embodiment, the outer wall surface of the flavor source container 31 includes the taper part 31T that becomes wide from the upstream to the downstream. Accordingly, the second cartridge 30 tends to fit in the outer frame 24 of the first cartridge 20, and drop out of the second cartridge 30 is suppressed while permitting manufacturing error of the outline of the flavor source container 31.

In the embodiment, in the predetermined direction A, a length L2 from the mesh body 32 to the downstream end portion of the rib 31R is shorter than a length L1 from the mesh body 32 to the downstream end portion of the flavor source container 31. In other words, the downstream end portion of the rib 31R comes into contact with the filter 33 without reaching the downstream end portion of the flavor source container 31. Accordingly, a function of positioning the filter 33 can be achieved while reinforcing the flavor source container 31 using the rib 31R.

First Modification

A first modification of the embodiment will be described below. Differences from the embodiment are mainly described below.

Specifically, in the embodiment, the flavor source container 31 has the protruding portion 31E (first protruding portion) as a spacer that forms the aerosol flow adjustment chamber G. Conversely, in the first modification, the flavor source container 31 does not have the protruding portion 31E.

Figure 19:
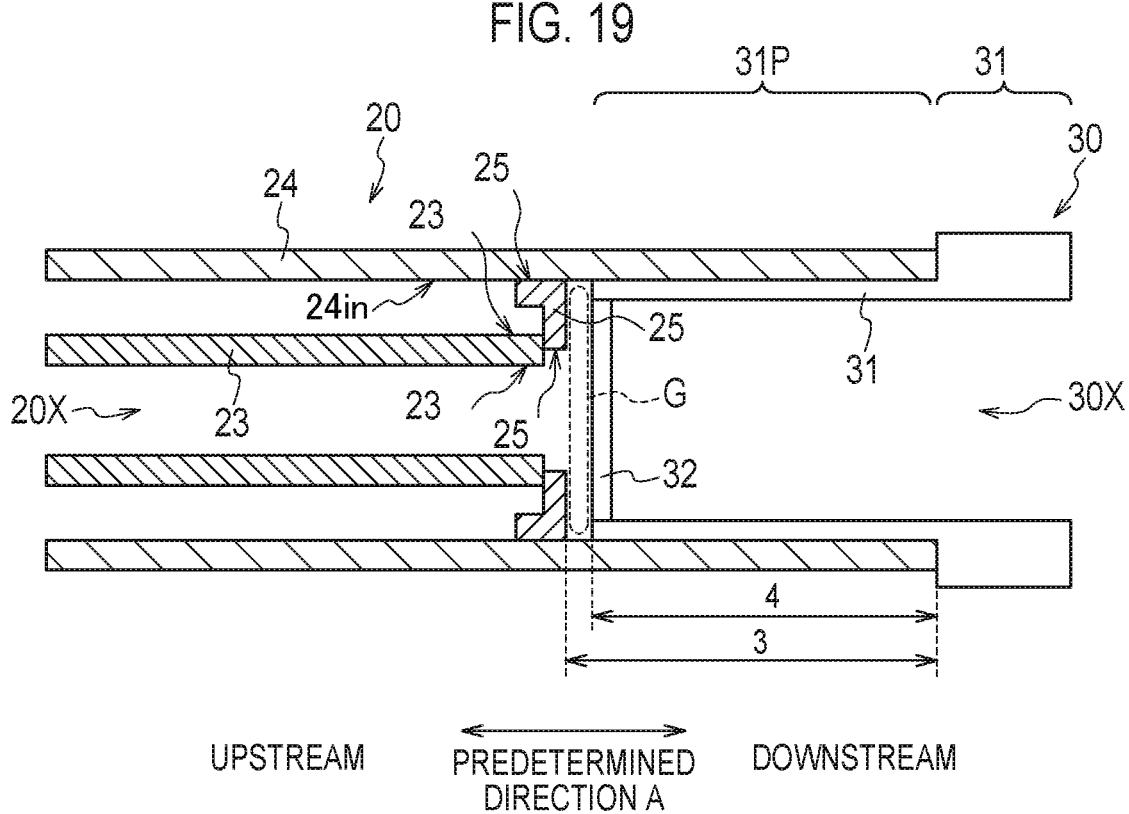
FIG. 19 is a diagram illustrating a connection state of the first cartridge 20 and the second cartridge 30 according to a first modification.

FIG. 19 is a diagram illustrating a connection state of the first cartridge 20 and the second cartridge 30 according to the first modification. However, it should be noted that in FIG. 19, the reservoir 21, the atomizer 22, the flavor source 31A, the filter 33, and the cap 34 are omitted.

As illustrated in FIG. 19, the flavor source container 31 has a main body portion 31P that accommodates the flavor source 31A and a flange portion 31Q provided on the side surface of the main body portion 31P. It should be noted that in the cross section orthogonal to the aerosol flow path (predetermined direction A), the flange portion 31Q overhangs to the outside than the main body portion 31P, and overhangs outside to the same degree or more as the inner surface of the outer frame 24. In FIG. 19, the flange portion 31Q is provided on the side surface of the downstream end portion of the main body portion 31P, but is not limited thereto, and may be provided somewhere on the side surface of the main body portion 31P in a mode of being locked to the inner surface of the outer frame 24.

Here, a distance L3 from the downstream end portion of the outer frame 24 to the end cap 25 (that is, a distance from a part in which the outer frame 24 abuts the flange portion 31Q to the downstream end portion of the end cap 25) is longer than a length L4 of the main body portion 31P (that is, a distance from an upstream end portion of the flange portion 31Q to the upstream end portion of the main body portion 31P). Accordingly, the aerosol flow adjustment chamber G that adjusts the flow of aerosol supplied from first flow path 20X is formed even if the flavor source container 31 does not have the protruding portion 31E by the flange portion 31Q catching on the downstream end portion of the outer frame 24.

Note that, when the first cartridge 20 does not have the end cap 25, a distance from the downstream end portion of the outer frame 24 to the downstream end portion of the flow path forming body 23 (that is, a distance from a part in which the outer frame 24 abuts the flange portion 31Q to the downstream end portion of the flow path forming body 23) is longer than a length of the main body portion 31P (that is, a distance from an upstream end portion of the flange portion 31Q to the upstream end portion of the main body portion 31P).

Second Modification

A second modification of the embodiment will be described below. Differences from the embodiment are mainly described below.

Specifically, in the embodiment, the flavor source container 31 has the protruding portion 31E (first protruding portion) as a spacer that forms the aerosol flow adjustment chamber G. Conversely, in the second modification, the flavor source container 31 does not have the protruding portion 31E.

Figure 20:
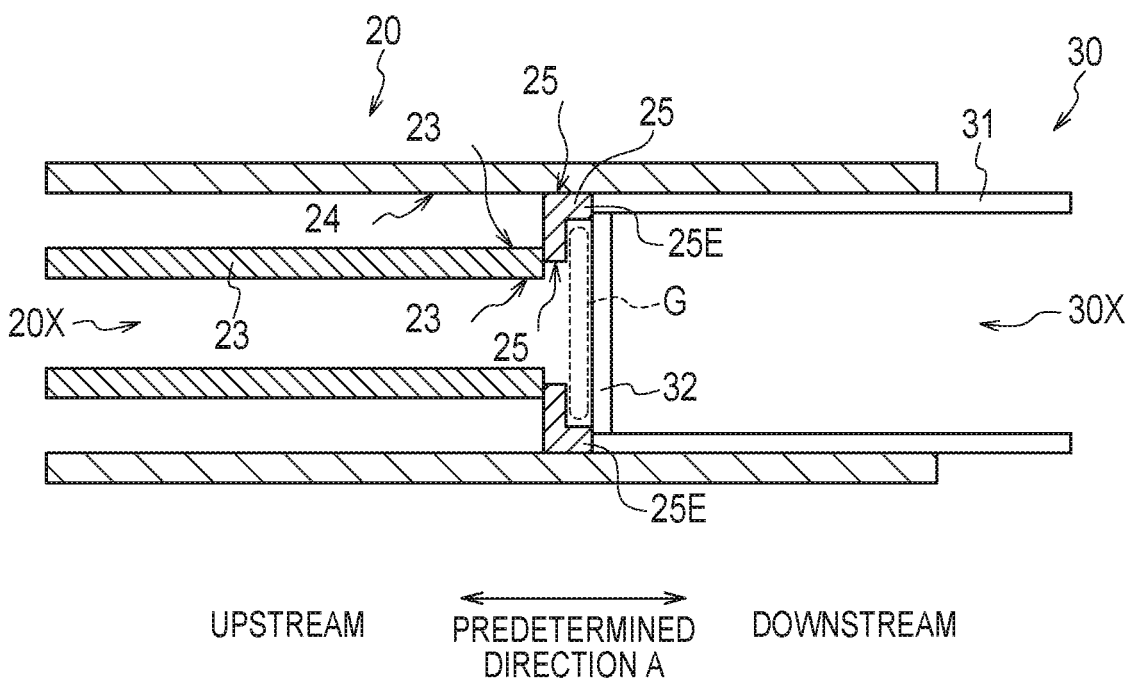
FIG. 20 is a diagram illustrating a connection state of the first cartridge 20 and the second cartridge 30 according to a second modification.

FIG. 20 is a diagram illustrating a connection state of the first cartridge 20 and the second cartridge 30 according to the second modification. However, it should be noted that in FIG. 20, the reservoir 21, the atomizer 22, the flavor source 31A, the filter 33, and the cap 34 are omitted. The protruding portion 25E contacts the upstream end portion of the flavor source container 31 (preferably, the outer edge of the upstream end portion).

As illustrated in FIG. 20, the end cap 25 has the protruding portion 25E that protrudes from the outer edge of the downstream end portion of the end cap 25 to the downstream side (flavor source container 31 side) in the cross section orthogonal to the aerosol flow path (predetermined direction A). The protruding portion 25E may be continuously provided along the outer edge of the end cap 25 and may be intermittently provided along the outer edge of the end cap 25. Note that, when there is a gap between the outer frame 24 and the flavor source container 31, preferably the protruding portion 25E is continuously provided along the outer edge of the end cap 25. Thereby, it is possible to suppress retention of aerosol in the gap formed in the upstream part of a taper part 31T.

In this manner, the aerosol flow adjustment chamber G that adjusts the flow of the aerosol supplied from first flow path 20X is formed even if the flavor source container 31 does not have the protruding portion 31E by the protruding portion 25E being provided in place of the protruding portion 31E.

Note that, when the first cartridge 20 does not have the end cap 25, the flow path forming body 23 has the same protruding portion as the protruding portion 25E that protrudes from the outer edge of the downstream end portion of the flow path forming body 23 to the downstream side (flavor source container 31 side) in the cross section orthogonal to the aerosol flow path (predetermined direction A).

Third Modification

A third modification of the embodiment will be described below. Differences from the embodiment are mainly described below.

Specifically, in the embodiment, the first flow path 20X completely overlaps the second flow path 30X viewed from the predetermined direction A. In addition, in the cross section orthogonal to the aerosol flow path (predetermined direction A), preferably the size of the second flow path 30X is larger than the size of the first flow path 20X.

Figure 21:
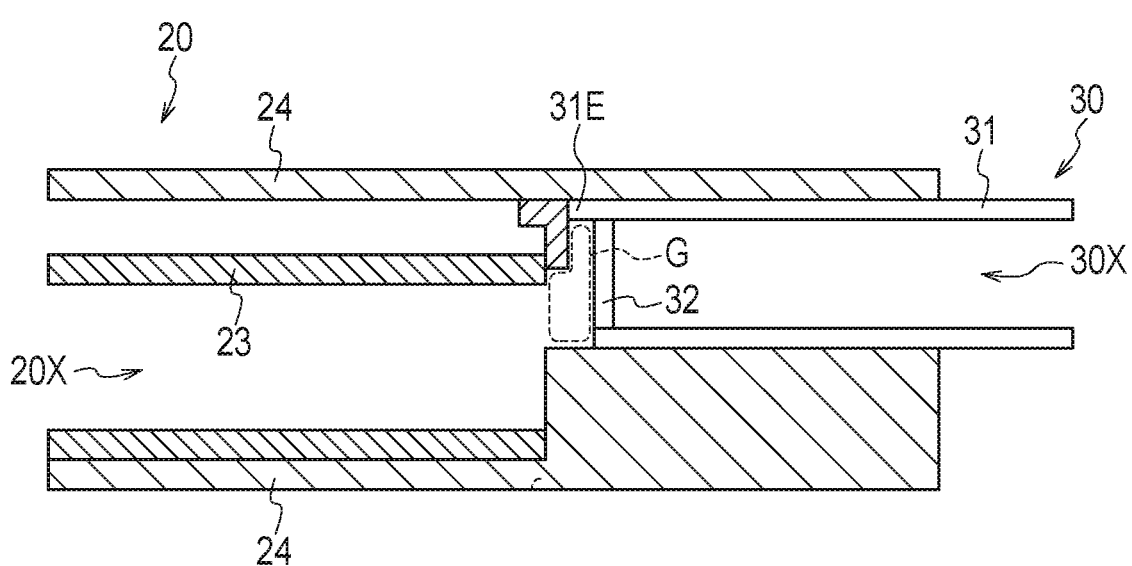
FIG. 21 is a diagram illustrating a connection state of the first cartridge 20 and the second cartridge 30 according to a third modification.

In contrast, in the third modification, as illustrated in FIG. 21, viewed from the predetermined direction A, the first flow path 20X is shifted from the second flow path 30X without completely overlapping the second flow path 30X. In such a case, in the cross section orthogonal to the aerosol flow path (predetermined direction A), the size of the second flow path 30X is not particularly limited, but may be to the same degree as the size of the first flow path 20X, and may be smaller than the size of the first flow path 20X. However, the size of the second flow path 30X may be larger than the size of the first flow path 20X.

Fourth Modification

Hereinafter, the fourth modification of the embodiment will be described with reference to FIG. 22 to FIG. 25. Differences from the embodiment are mainly described below. In FIG. 22 to FIG. 25, the vertical axis represents the aerosol amount (amount of total particulate matter (TPM)) (mg/puff action), and the horizontal axis represents the number of puff actions (puff number). The vertical axis and the horizontal axis represent larger values as it is away from the intersection point of both axes.

In the fourth modification, in the same manner as in the embodiment, the power controller 53 stops power supply from the battery 11 to the atomizer 22 when a predetermined period elapses from the start of power supply to the atomizer 22. The predetermined period is shorter than an upper limit value of a standard puff period derived from statistics of puff periods of users.

Note that, the aerosol amount atomized by the atomizer 22 depends on the puff period in which the puff action is actually performed by the user and the output voltage output to the battery 11. Here, the explanation may be given assuming that the standard puff period derived from statistics of the puff period of the user may be considered as following a normal distribution having an average of 2.4 seconds and a standard deviation of 1 second. Note that, in such a case, as described above, the upper limit value of the standard puff period is derived as m+nσ (here, m is the average value, σ is standard deviation, and n is a positive real number), and for example, is to the degree of three to four seconds. Here, description is made assuming a case in which the upper limit value of the standard puff period is three seconds (n=0.6).

Figure 22:
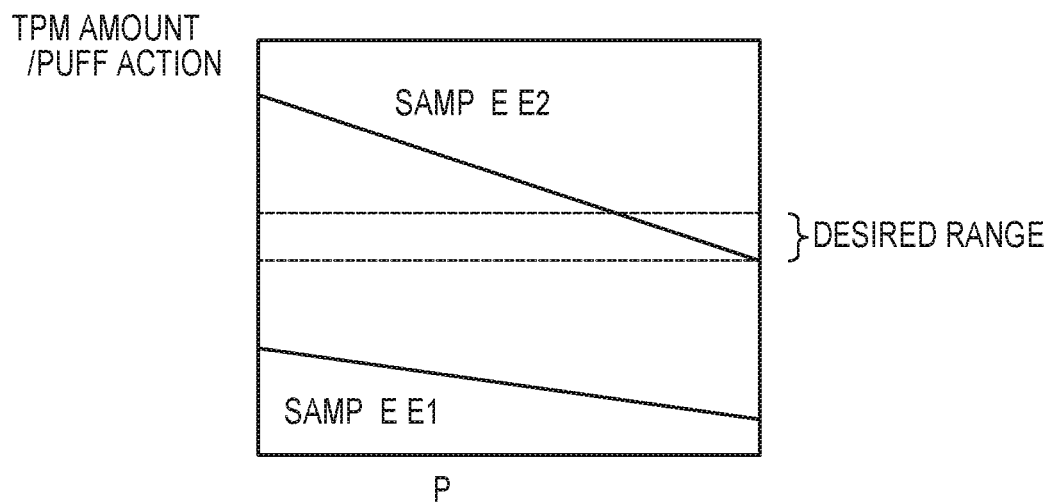
FIG. 22 is a diagram for explaining an aerosol amount according to a fourth modification.

In sample E, an initial value of the output voltage of the battery 11 is 4.2 V, and the battery capacity of the battery 11 is 220 mAh. In addition, the atomizer 22 is constituted by the heating wire wound around, and the resistance value of the heating wire is 3.5Ω. In FIG. 22, a sample E1 indicates a relationship between the number of puffs and the aerosol amount when sample E is inhaled in the puff period of two seconds per one puff action, and a sample E2 indicates the relationship between the number of puffs and the aerosol amount when sample E is inhaled in the puff period of three seconds per one puff action. Here, it should be noted that when the standard puff period follows an average of 2.4 seconds and normal distribution of the standard deviation of one second, probability of inhaling in the puff period of three seconds or more per one puff action as indicated in sample E2 is approximately 27%, and is a circumstance that sufficiently occurs.

Figure 23:
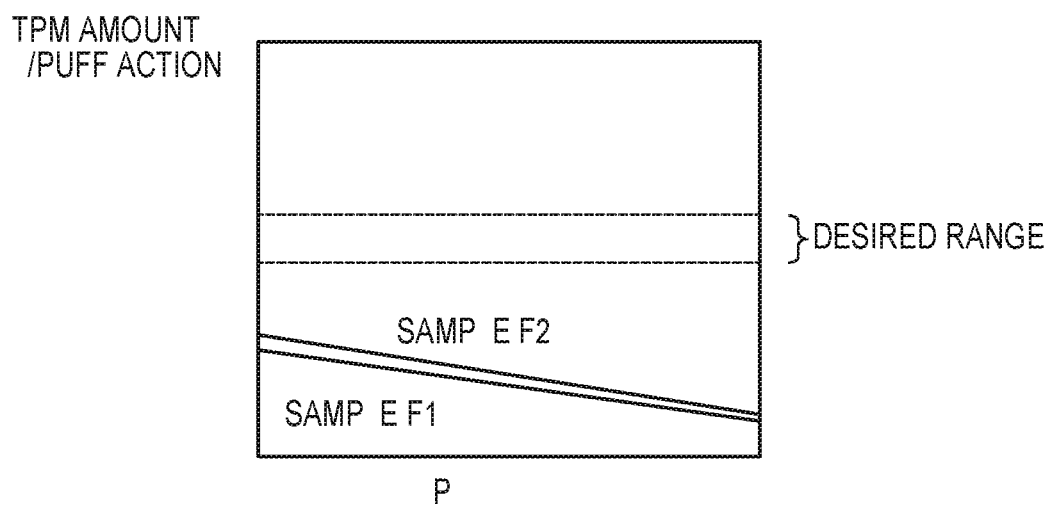
FIG. 23 is a diagram for explaining the aerosol amount according to the fourth modification.

In sample F, the configuration of the battery 11 and the atomizer 22 is the same as the sample E. In FIG. 23, a sample F1 indicates a relationship between the number of puffs and the aerosol amount when sample F is inhaled in the puff period of two seconds per one puff action, and a sample F2 indicates the relationship between the number of puffs and the aerosol amount when sample F is inhaled in the puff period of three seconds per one puff action. However, in the sample F1 and the sample F2, the power controller 53 stops power supply from the battery 11 to the atomizer 22 when a predetermined period elapse from the start of power supply to the atomizer 22 (here, 2.2 seconds). Here, it should be noted that the predetermined period is 2.2 seconds that is shorter than the upper limit value of the standard puff period derived from statistics of the puff period of the user, and is shorter than the average value of the puff period.

Figure 24:
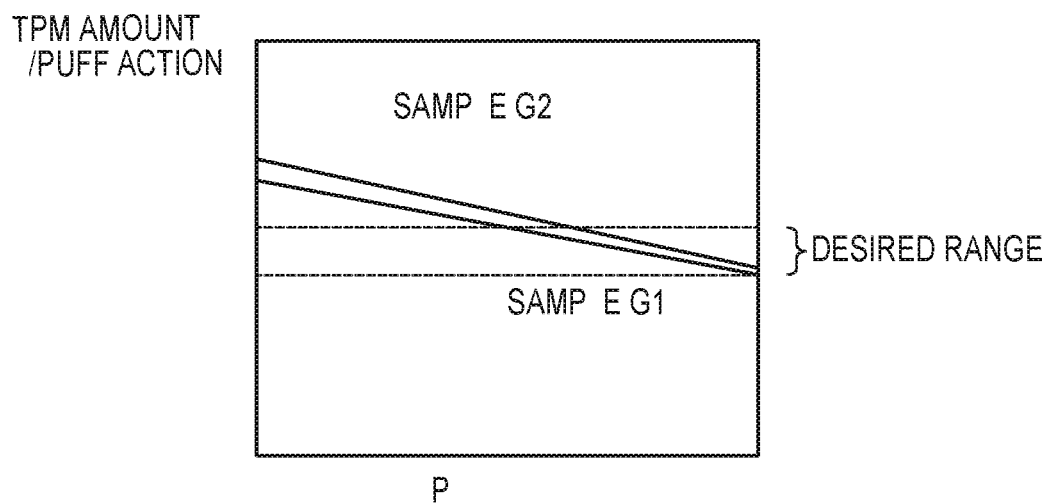
FIG. 24 is a diagram for explaining the aerosol amount according to the fourth modification.

In a sample G, the configuration of the battery 11 is the same as the samples E and F. Meanwhile, the atomizer 22 is constituted by the heating wire wound at a predetermined pitch, and is different from samples E and F in that the resistance value of the heating wire is 2.9Ω. In FIG. 24, a sample G1 indicates a relationship between the number of puffs and the aerosol amount when the sample G is inhaled in the puff period of two seconds per one puff action, and a sample G2 indicates the relationship between the number of puffs and the aerosol amount when the sample G is inhaled in the puff period of three seconds per one puff action. However, in the sample G1 and the sample G2, the power controller 53 stops power supply from the battery 11 to the atomizer 22 when a predetermined period elapse from the start of power supply to the atomizer 22 (here, 2.2 seconds).

Figure 25:
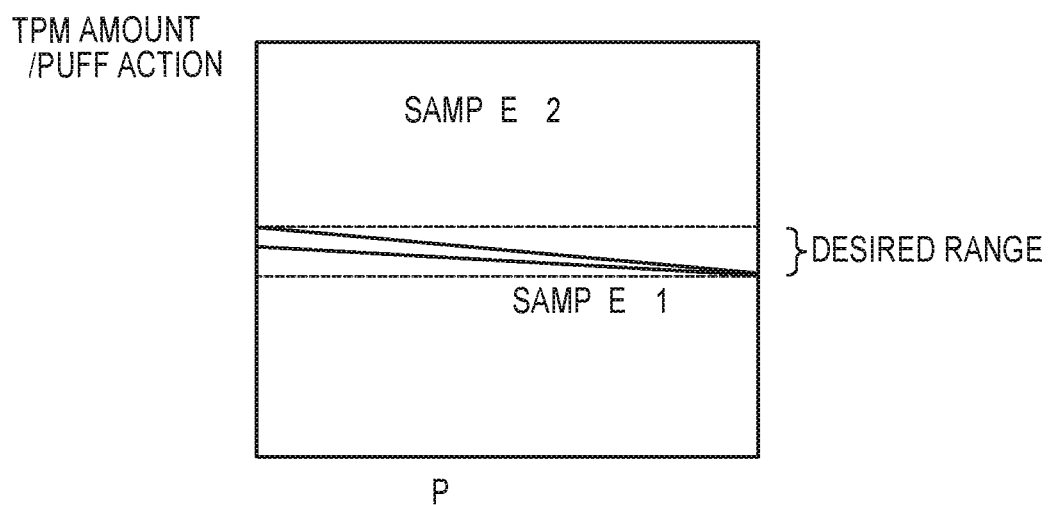
FIG. 25 is a diagram for explaining the aerosol amount according to the fourth modification.

In a sample H, the configuration of the battery 11 and the atomizer 22 is the same as the sample G. However, the predetermined pitch of the heating wire forming the atomizer 22 is uniformly wound in a range of from 0.35 to 0.40 mm, and is narrower than the predetermined pitch of the sample G. In FIG. 25, a sample H1 indicates a relationship between the number of puffs and the aerosol amount when the sample H is inhaled in the puff period of two seconds per one puff action, and a sample H2 indicates the relationship between the number of puffs and the aerosol amount when the sample H is inhaled in the puff period of three seconds per one puff action. In addition, in the sample H1 and the sample H2, in the same manner as the sample G, the power controller 53 stops power supply from the battery 11 to the atomizer 22 when a predetermined period elapse from the start of power supply to the atomizer 22 (here, 2.2 seconds). However, in the sample H1 and the sample H2, the duty ratio is modified during power supply to the atomizer 22 according to the value of the output voltage of the battery 11 detected by the detector 51. Specifically, as described above, since the output voltage of the battery 11 lowers accompanying reduction of the accumulated amount in the battery 11, the duty ratio of the power supplied to the atomizer 22 is increased according to lowering of the output voltage of the battery 11.

Under such premises, as illustrated in FIG. 22, the sample E in which the puff period and the energization time to the atomizer 22 match regardless of the length of the puff period is modified such that the aerosol amount is large when the puff period is three seconds and when the puff period is two seconds. In addition, as understood by comparing inclination of the sample E1 and the sample E2, variation of the aerosol amount from the initial puff up to the final puff is more remarkable the longer the puff period, that is, the energization time.

Focusing on such results, an inventor and the like found that when the predetermined period is set shorter than the upper limit value of the standard puff period derived from statistics of the puff period of the user and the predetermined period elapses from the start of power supply to the atomizer 22 in one puff action, as illustrated in FIG. 23, it is possible to suppress variation of the aerosol amount from the initial puff up to the final puff even in the sample F2 in which the puff period is three seconds by stopping power supply from the battery 11 to the atomizer 22. Thereby, it is possible to suppress variation of the aerosol amount because of variation of the puff period of the user.

Furthermore, focusing on such results, as illustrated in FIG. 24, the inventor and the like found that it is possible for the aerosol amount atomized by the atomizer 22 falls within the desired range across the number of longer puffs from the initial puff to the final puff by modifying the configuration of the atomizer 22 such that the aerosol amount atomized by the atomizer 22 falls within the desired range when the energization time of the atomizer 22 is the predetermined period. Here, comparing the sample G2 illustrated in FIG. 24 and the sample F2 illustrated in FIG. 23, in the sample G2, the aerosol amount atomized by the atomizer 22 falls within the desired range across the number of puffs that are longer than the sample F2, whereas a fluctuation range of the aerosol amount from the initial puff to the final puff is increased more than the fluctuation range in the sample F2. Thereby, the amount of power supply from the battery 11 to the atomizer 22 increases in one puff action by modifying the configuration of the atomizer 22.

Furthermore, focusing on such results, the inventor and the like found that it is possible to mitigate a reduction rate of the aerosol amount by carrying out the following modifications. Specifically, it is possible to mitigate the reduction rate of the aerosol amount by increasing the duty ratio of the power supplied to the atomizer 22 in response to lowering of the output voltage of the battery 11. In addition, it is possible to mitigate the reduction rate of the aerosol amount even if the predetermined pitch of the heating wire is narrow. As illustrated in FIG. 25, by such a modification, it was found that the aerosol amount atomized by the atomizer 22 falls within the desired range across the entire period from the initial puff to the final puff in either of H1 in which the puff period is two seconds and H2 in which the puff period is three seconds.

Based on these results, the inventor and the like newly found that it is effective to perform control as indicated below on the power supply from the battery 11 to the atomizer 22.

(1) The power controller 53 stops power supply from the battery 11 to the atomizer 22 when a predetermined period elapses from the start of power supply to the atomizer 22. Here, preferably the predetermined period is shorter than the upper limit value of the standard puff period derived from statistics of the puff period of the user, and is shorter than the average value of the puff period.

(2) The resistance value of the heating wire of the atomizer 22 is determined such that the aerosol amount in the desired range is atomized when the energization time of the atomizer 22 is the predetermined period. Here, preferably the resistance value of the heating wire is determined such that the voltage supplied from the battery 11 to the atomizer 22 is set as the voltage in the final stage in which the accumulated amount in the battery 11 is insufficient and the aerosol amount atomized by the atomizer 22 falls within the desired range when the energization time of the atomizer 22 is the predetermined period.

(3) Furthermore, the power controller 53 increases the duty ratio of power supplied to the atomizer 22 in response to a reduction of the output voltage of the battery 11 such that the aerosol amount atomized by the atomizer 22 falls within the desired range across the entire period from the initial puff to the final puff.

By the control described above, regardless of the length of the puff period of the user, it is possible to suppress a difference of the amount of power actually supplied from the battery 11 to the atomizer 22, through the initial step, in which the accumulated amount in the battery 11 is sufficient, to the final step, in which the accumulated amount in the battery 11 is insufficient, and it is easy for the aerosol amount to fall within the desired range.

That is, in the fourth modification, the atomizer 22 is configured to be capable of atomizing the aerosol of a larger amount than the desired range of the amount of supply of the aerosol in one puff action at the start of use of at least the atomizer 22 (in other words, while the battery 11 is fully charged) by adjusting the predetermined pitch of the heating wire forming the atomizer 22 and the resistance value.

Under such premises, the predetermined instruction (here, duty ratio) output from the power controller 53 is determined based on the length of the predetermined period such that the aerosol amount atomized by the atomizer 22 in the predetermined period falls within the desired range. In other words, the predetermined instruction is determined based on the length of the predetermined period in a state in which variance of the aerosol amount caused by the variance of the length of the puff period of the user is suppressed by determining the predetermined period. Accordingly, it is possible for the aerosol amount to easily fall in the desired range regardless of the length of the puff period of the user from the initial step (start of smoking) in which the accumulated amount in the battery 11 is sufficient up to the final step (end of smoking) in which the accumulated amount in the battery 11 is insufficient.

In the fourth modification, preferably the upper limit of the aerosol amount (desired range) atomized by the atomizer 22 is 4.0 mg per one puff action. Furthermore, preferably the upper limit is 3.0 mg per one puff action. Deterioration of the raw material pieces included in the flavor source 31A accommodated in the second cartridge 30 is suppressed by the value described above being the upper limit.

Meanwhile, preferably the lower limit of the aerosol amount (desired range) atomized by the atomizer 22 is 0.1 mg per one puff action. By setting the value described above to the lower limit, it is possible to supply the aerosol to the user at an amount that does not impart a sense of shortage, and it is possible to remove the flavor component from the flavor source 31A accommodated in the second cartridge 30 using the aerosol.

Fifth Modification

A fifth modification of the embodiment will be described below. Differences from the embodiment are mainly described below.

In the embodiment described above, the predetermined period is determined according to the standard puff period derived from statistics of the puff periods of the plurality of users. In contrast, in the fifth modification, the predetermined period is derived from statistics of the puff period of the user who actually uses the non-burning type flavor inhaler 1.

Figure 26:
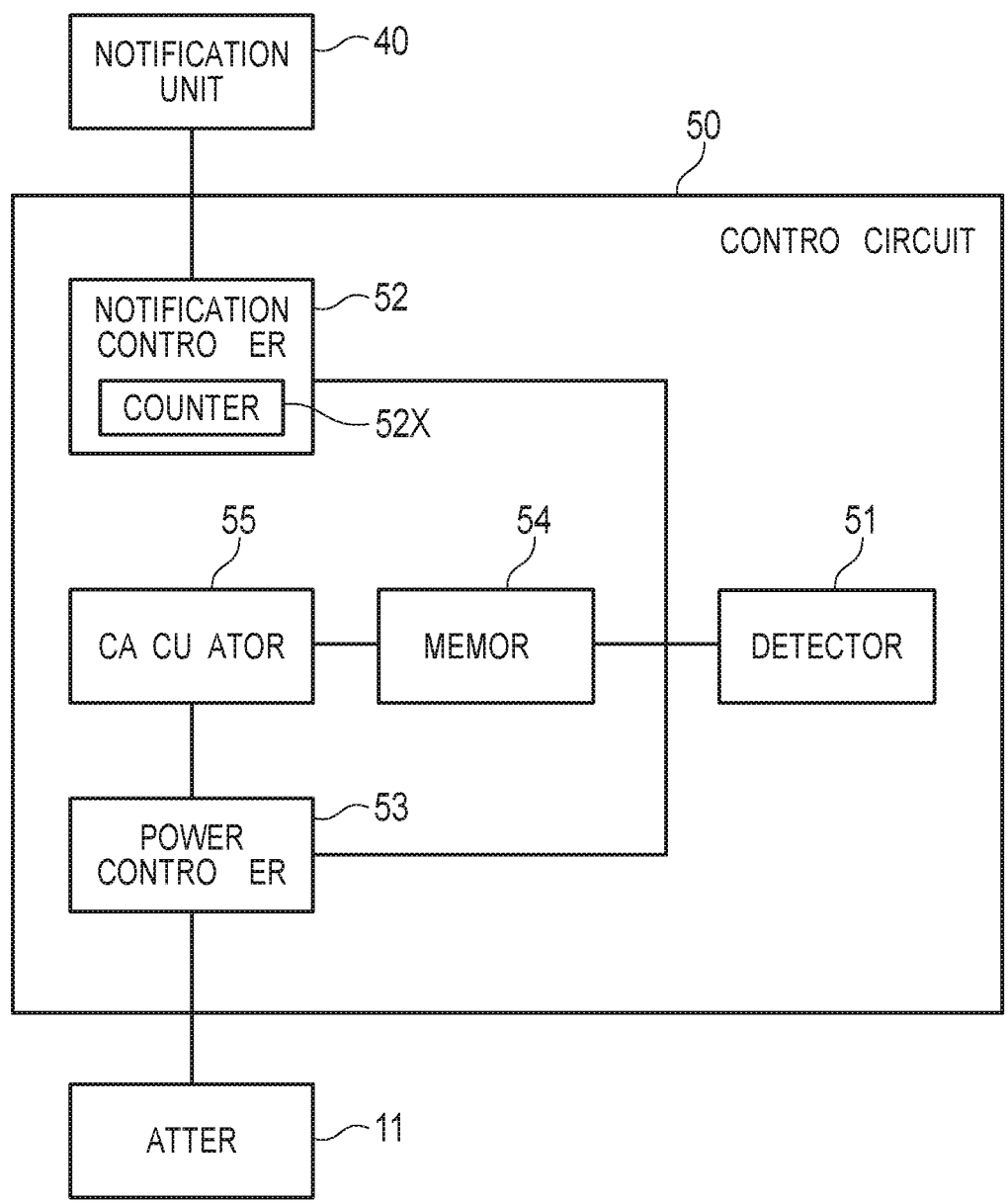
FIG. 26 is a diagram mainly illustrating a function block of a control circuit 50 according to a fifth modification.

FIG. 26 is a diagram mainly illustrating a function block of the control circuit 50 according to the fifth modification. In FIG. 26, the same reference numerals are given to the same configuration as in FIG. 15, and description of the same configuration as in FIG. 15 is omitted.

As illustrated in FIG. 26, the control circuit 50 has a memory 54 and a calculator 55 in addition to the configuration illustrated in FIG. 15.

The memory 54 stores the puff period that is a period in which the user performs the puff action.

The calculator 55 calculates the predetermined period described above from statistics of the puff period stored in the memory 54. That is, the predetermined period is derived from statistics of the puff period stored in the memory 54. However, it should be noted that the predetermined period is shorter than the upper limit of the standard puff period described above.

For example, the calculator 55 operates the predetermined period in the following procedures.

Firstly, in the same manner as in the embodiment described above, in the initial setting, the predetermined period (I seconds) is determined in advance according to the standard puff period derived from statistics of the puff periods of the plurality of users.

Secondly, for example, the average value is derived from statistics of the puff period detected in a fixed period (for example, from the start of use of the first cartridge 20 up to replacement of the first cartridge 20).

Thirdly, the predetermined period is modified to the average value (X seconds).

Fourthly, the duty ratio is modified such that the amount of power supply to the atomizer 22 during inhaling for X seconds is equal to the amount of power supply during initial setting (during inhaling for I seconds). That is, when the average value (X)<initial setting value (I), the duty ratio that corresponds to each battery voltage is relatively increased. Meanwhile, when the average value (X)>initial setting value (I), the duty ratio is reduced.

Note that, preferably for example, the predetermined period is recalculated in each fixed period (for example, replacement of the first cartridge 20).

(Operation and Effect)

In the fifth modification, the predetermined period is derived from statistics of the puff period of the user who actually uses the non-burning type flavor inhaler 1. Accordingly, it is possible to set a period appropriate to the user as the predetermined period referenced when stopping the power supply from the battery 11 to the atomizer 22. More particularly, it is possible to mitigate discomfort because of supply of the aerosol across the entirety of the puff period applied to the user who has a long puff period, and it is possible to increase the number of puff actions in which aerosol is supplied in the desired range to a user who has a short puff period compared to a case in which the predetermined period derived from statistics of the puff periods of a plurality of users is used by setting the predetermined period appropriate in the actual puff period of the user.

Sixth Modification

A sixth modification of the embodiment will be described below. Differences from the embodiment are mainly described below.

In the embodiment described above, the predetermined period is determined according to the standard puff period derived from statistics of the puff periods of the plurality of users. In contrast, in the sixth modification, the predetermined period is derived from statistics of the puff period of the user who actually uses the non-burning type flavor inhaler 1.

Figure 27:
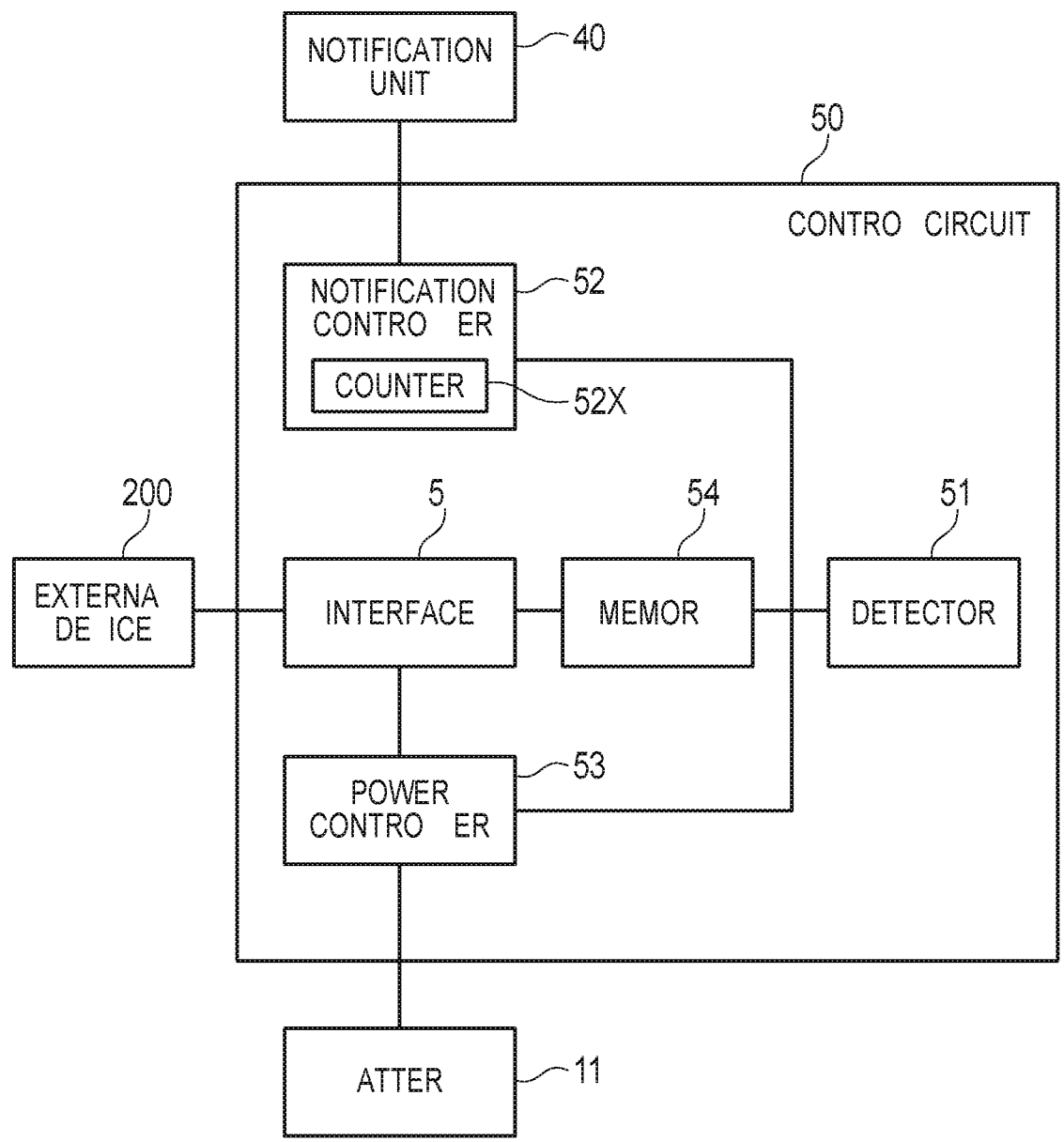
FIG. 27 is a diagram mainly illustrating a function block of a control circuit 50 according to a sixth modification.

FIG. 27 is a diagram mainly illustrating a function block of the control circuit 50 according to the sixth modification.

In FIG. 27, the same reference numerals are given to the same configuration as in FIG. 15, and description of the same configuration as in FIG. 15 is omitted.

As illustrated in FIG. 27, the control circuit 50 has a memory 54 and an interface 56 in addition to the configuration illustrated in FIG. 15.

The memory 54 stores the puff period a period in which the user performs the puff action.

The interface 56 is an interface for communicating with an external device 200 provided separately from the non-burning type flavor inhaler 1. The interface 56 may be a USB port, may be a wired LAN module, may be a wireless LAN module, and may be a near field communication module (for example, Bluetooth or FeliCa). The external device 200 may be a personal computer, and may be a smartphone.

Specifically, the interface 56 transmits the puff period stored in the memory 54 to the external device 200. The interface 56 receives the predetermined period calculated from statistics from the external device 200 based on the puff period using the external device 200.

It should be noted that the external device 200 calculates the predetermined period using the same method as the calculator 55 according to the fifth modification.

(Operation and Effect)

In the sixth modification, the predetermined period is derived from statistics of the puff period of the user who actually uses the non-burning type flavor inhaler 1. Accordingly, it is possible to set a period appropriate to the user as the predetermined period referenced when stopping the power supply from the battery 11 to the atomizer 22. More particularly, it is possible to mitigate discomfort because of supply of the aerosol across the entirety of the puff period applied to the user who has a long puff period, and it is possible to increase the number of puff actions in which aerosol is supplied in the desired range to a user who has a short puff period compared to a case in which the predetermined period derived from statistics of the puff periods of a plurality of users is used by setting the predetermined period appropriate in the actual puff period of the user.

Seventh Modification

A seventh modification of the embodiment will be described below. Differences from the embodiment are mainly described below.

Figure 28:
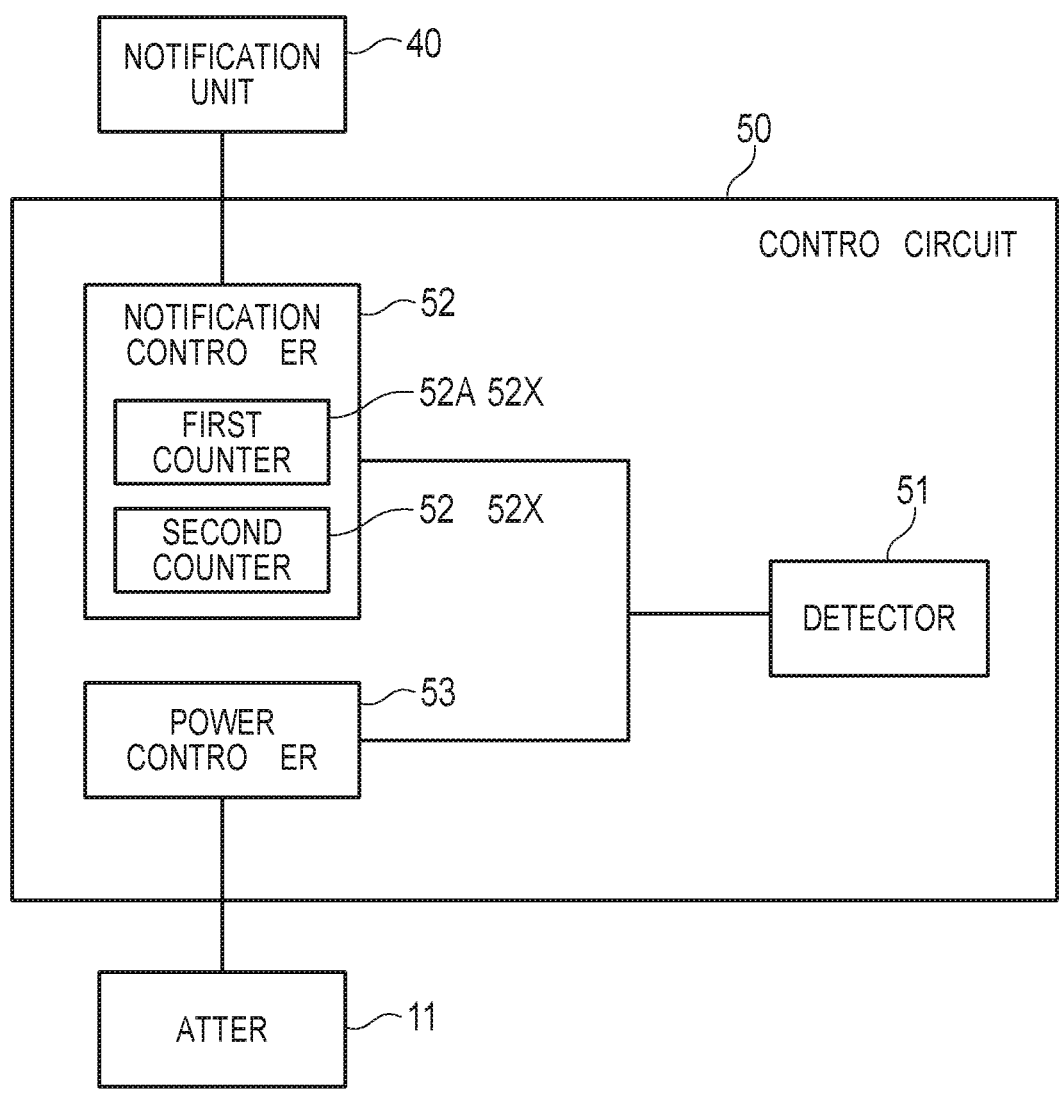
FIG. 28 is a diagram mainly illustrating a function block of a control circuit 50 according to a seventh modification.

In the embodiment described above, the notification controller 52 has the counter 52X that counts the number of puff actions or the energization time of the atomizer 22. In contrast, in the seventh modification, as illustrated in FIG. 28, the notification controller 52 has a first counter 52A and a second counter 52B as the counter 52X that counts the number of puff actions or the energization time of the atomizer 22.

In the seventh modification, it should be noted that the lifespan of the first cartridge 20 is the lifespan of the second cartridge 30×T (T is an integer)+β. Note that, β is a value smaller than the lifespan of the second cartridge 30, but is not particularly limited thereto.

The notification controller 52 detects the replacement timing of the second cartridge 30 when the count value of the first counter 52A reaches a first predetermined value. The notification controller 52 detects the replacement timing of the first cartridge 20 when the count value of the second counter 52B reaches a second predetermined value. The second predetermined value is an integral multiple of the first predetermined value.

Alternatively, when the count value of the first counter 52A reaches a predetermined value P, the notification controller 52 may detect the replacement timing of the second cartridge 30 and increment the count value of the second counter 52B. Thereby, the notification controller 52 may detect the replacement timing of the first cartridge 20 when the count value of the second counter 52B reaches a predetermined value Q. That is, in the same manner as in the embodiment described above, the notification controller 52 may detect the replacement timing of the first cartridge 20 when the number of replacement times of the second cartridge 30 reaches a predetermined number of times (predetermined value Q).

In this manner, it should be noted that as a result of the second predetermined value being an integral multiple of the first predetermined value, the notification controller 52 detects the replacement timing of the first cartridge 20 based on the number of times of replacement of the second cartridge 30.

In the seventh modification, when the count value of the first counter 52A reaches the first predetermined value, the notification controller 52 may detect the replacement timing of the second cartridge 30 and reset the count value of the first counter 52A. Alternatively, when the count value of the first counter 52A reaches the first predetermined value, the notification controller 52 may detect the replacement timing of the second cartridge 30 and reset the count value of the first counter 52A according to the predetermined operation of the user. In such a case, preferably the power controller 53 stops the power supply from the battery 11 to the atomizer 22 from the count value of the first counter 52A reaching the first predetermined value until the count value is reset.

In the seventh modification, when the count value of the second counter 52B reaches the second predetermined value, the notification controller 52 may detect the replacement timing of the first cartridge 20 and reset the count value of the second counter 52B. Alternatively, when the count value of the second counter 52B reaches the second predetermined value, the notification controller 52 may detect the replacement timing of the first cartridge 20 and reset the count value of the second counter 52B according to the predetermined operation of the user. In such a case, preferably the power controller 53 stops the power supply from the battery 11 to the atomizer 22 from the count value of the second counter 52B reaching the second predetermined value until the count value is reset.

(Operation and Effect)

In the seventh modification, it is possible to improve convenience for the user by notifying the replacement timing of the first cartridge 20 and the second cartridge 30 at the same timing even when replacement of the second cartridge 30 is repeated because the second predetermined value is an integral multiple of the first predetermined value.

Eighth Modification

An eighth modification of the embodiment will be described below. Differences from the embodiment are mainly described below.

Figure 29:
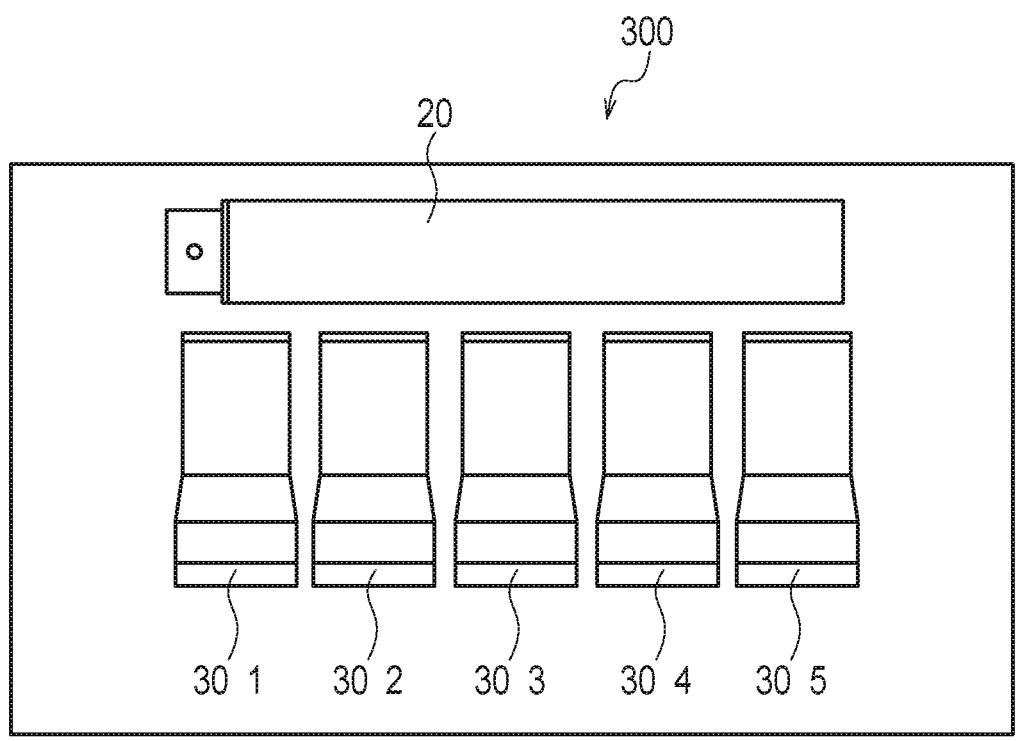
FIG. 29 is a diagram illustrating a package 300 according to an eighth modification.

In the eighth modification, a package provided with the first cartridge and the second cartridge is described. FIG. 29 is a diagram illustrating a package 300 according to the eighth modification.

As described in FIG. 29, the package 300 has the first cartridge 20 and the second cartridge 30. The number of second cartridges 30 is determined according to the lifespan of the first cartridge 20. For example, the package 300 illustrated in FIG. 29 has one first cartridge 20 and five second cartridges 30. In other words, the number of second cartridges 30 is determined such that the lifespan of one first cartridge 20 comes to an end when five second cartridges 30 are used up.

Specifically, a permissible puff number that is the number of puff actions permissible for the first cartridge 20 or a permissible energization time that is the energization time permitted in the first cartridge 20 is determined for the first cartridge 20. The number of permissible puffs and the permissible energization time are values for suppressing depletion of the aerosol source 21A. In other words, the number of permissible puffs or the permissible energization time is upper limit value allows to atomize appropriate aerosol while stably supplying the aerosol source 21A to the atomizer 22. A timing at which the number of puff actions or the energization time of the atomizer 22 reaches the predetermined value is determined as the replacement timing of the second cartridge 30. The number of second cartridges 30 is an integral part of a quotient in which the permissible puff number or the permissible energization time is divided by the predetermined value. Here, the permissible puff number or the permissible energization time may not be divided by the predetermined value. In other words, the lifespan of the first cartridge 20 may be a lifespan that has a margin with respect to the number of second cartridges 30.

Alternatively, a timing at which the number of puff actions or the energization time of the atomizer 22 reaches the first predetermined value is the replacement timing of the second cartridge 30. A timing at which the number of puff actions or the energization time of the atomizer 22 reaches the second predetermined value is the replacement timing of the first cartridge 20. The second predetermined value is an integral multiple T of the first predetermined value. The integral multiple T is the number of the second cartridges 30 that are contained in the package 300.

(Operation and Effect)

In the eighth modification, convenience for the user is improved since the replacement timing of the first cartridge 20 and the second cartridge 30 are aligned even when replacement of the second cartridge 30 is repeated since the number of second cartridges 30 is determined according to the lifespan of the first cartridge 20. In other words, it is possible for the user to easily ascertain the replacement timing of the first cartridge 20 by using up the second cartridge 30 contained in the package 300.

Ninth Modification

A ninth modification of the embodiment will be described below. Main differences from the embodiment are described below.

In the ninth modification, the power controller 53 carries out a detection process in which the replacement timing of the second cartridge 30 is detected when power supply from the battery 11 to the atomizer 22 is stopped. According to such a configuration, power supply from the battery 11 to the atomizer 22 is continuous even when an original timing at which the second cartridge 30 is to be replaced (for example, a timing at which an energization time to the atomizer 22 reaches the predetermined value) is included in the way of the puff action. In comparison to a case in which power supply from the battery 11 to the atomizer 22 is forcibly stopped at the original timing at which the second cartridge 30 is to be replaced, aerosol of a desired amount is able to be supplied in the final puff action and it is possible to mitigate discomfort imparted to the user.

In such a case, preferably the power controller 53 carries out the detection process from stopping of power supply from the battery 11 to the atomizer 22 until a determination period has elapsed. Here, preferably the determination period is a period that is assumed to be shorter than a period from the end of a current puff action until a subsequent puff action starts. As the determination period, for example, it is possible to use a period such as three seconds or one second. According to such a configuration, a circumstance is suppressed in which a possibility that the detection process is carried out until the subsequent puff starts is high and aerosol of the desired amount is not supplied in the subsequent puff action (final puff action).

In addition, preferably the notification controller 52 controls the notification unit 40 so as to notify the replacement timing of the second cartridge 30 from stopping of power supply from the battery 11 to the atomizer 22 until the determination period has elapsed (notification process) when the replacement timing of the second cartridge 30 is detected in the detection process. According to such a configuration, it is possible to prompt such that the possibility that the notification process is carried out up to the subsequent puff starting is high and the user does not start the subsequent puff action in which aerosol of the desired amount is not supplied.

However, preferably the power controller 53 carries out the detection process until power supply from the battery 11 to the atomizer 22 starts in response to the start of the puff action when the puff action starts from stopping of power supply from the battery 11 to the atomizer 22 until the detection process is carried out. In other words, preferably the power controller 53 carries out the detection process prior to resuming power supply from the battery 11 to the atomizer 22 in the subsequent puff action. According to such a configuration, at least a circumstance in which aerosol of the desired amount is not supplied in the subsequent puff action is suppressed. Note that, preferably the notification controller 52 carries out the notification process prior to resuming power supply from the battery 11 to the atomizer 22 in the subsequent puff action when the replacement timing of the second cartridge 30 is detected in the detection process.

(Control Method)

Figure 30:
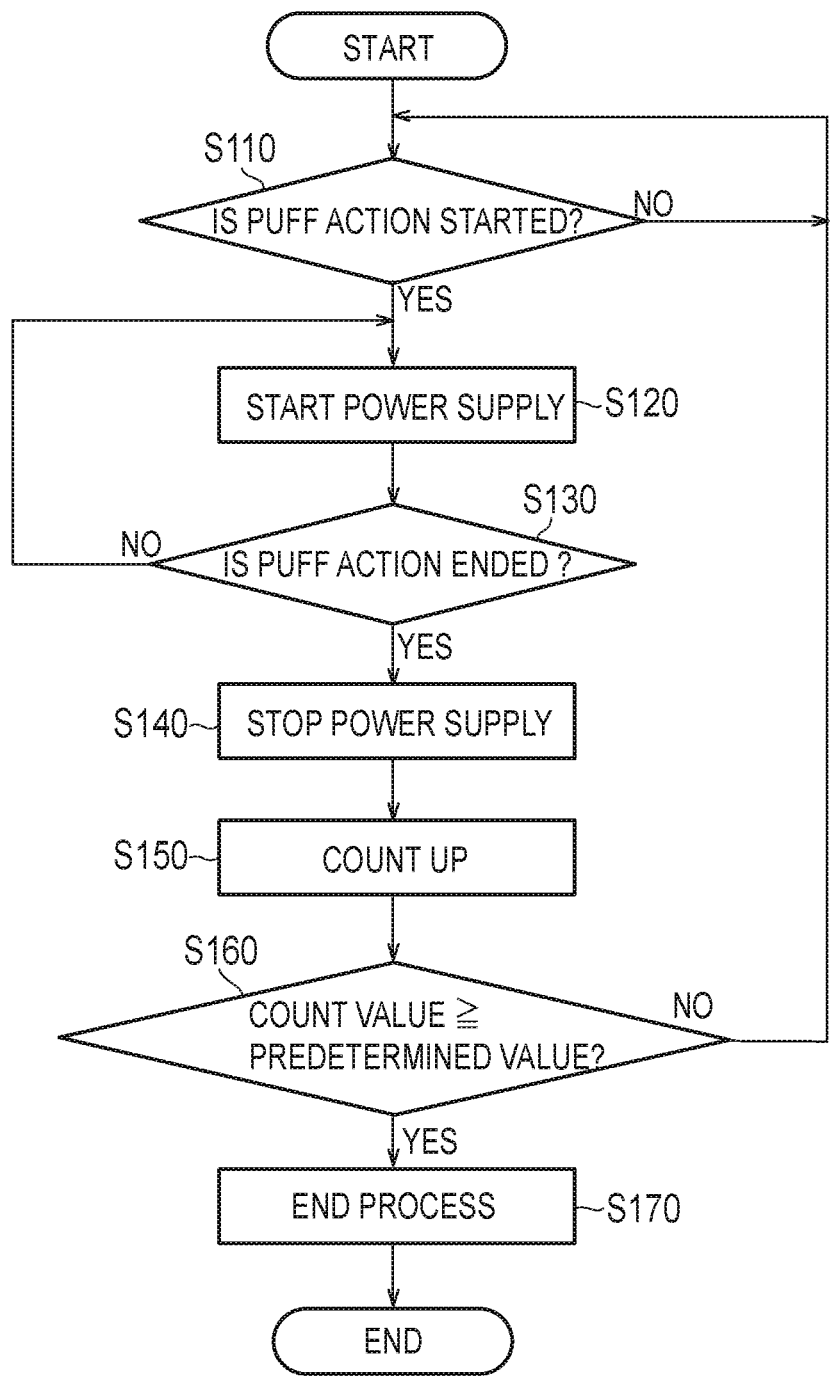
FIG. 30 is a flowchart illustrating a control method according to a ninth modification.

A control method according to the ninth modification will be described below. FIG. 30 is a flowchart illustrating the control method according to the embodiment. FIG. 30 is a flowchart illustrating the control method of the amount of power supplied from the battery 11 to the atomizer 22 in one puff action.

As illustrated in FIG. 30, in step S110, the non-burning type flavor inhaler 1 (that is, the control circuit 50, hereinafter the same) determines whether or not the start of the puff action is detected. If a determination result is YES, the non-burning type flavor inhaler 1 transitions to a process of step S120. If a determination result is NO, the non-burning type flavor inhaler 1 is in a standby state.

In step S120, the non-burning type flavor inhaler 1 starts power supply to the atomizer 22. In the same manner as in the embodiment, the non-burning type flavor inhaler 1 outputs to the battery 11 a predetermined instruction instructed to the battery 11 such that the aerosol amount atomized by the atomizer 22 falls in the desired range.

In step S130, the non-burning type flavor inhaler 1 determines whether or not the end of the puff action is detected. If a determination result is YES, the non-burning type flavor inhaler 1 transitions to a process of step S140. If a determination result is NO, the non-burning type flavor inhaler 1 is in a standby state. However, in the same manner as in the embodiment, the non-burning type flavor inhaler 1 may stop power supply to the atomizer 22 also in the puff period in which the puff action is actually performed by the user when the predetermined period from the start of power supply to the atomizer 22 has elapsed.

In step S140, the non-burning type flavor inhaler 1 stops power supply to the atomizer 22.

In step S150, the non-burning type flavor inhaler 1 counts up the counter 52X. In the same manner as in the embodiment, the counter 52X may count the number of puff actions and may count the energization time of the atomizer 22.

In step S160, the non-burning type flavor inhaler 1 determines whether or not the count value of the counter 52X reaches the predetermined value. If a determination result is YES, the non-burning type flavor inhaler 1 transitions to a process of step S170. When the determination result is NO, the non-burning type flavor inhaler 1 returns to the process of step S110.

In step S170, the non-burning type flavor inhaler 1 carries out the end process. For example, the end process may be a process in which the replacement timing of the second cartridge 30 is notified from the notification unit 40 and may be a process in which the power source of the non-burning type flavor inhaler 1 is forcibly switched off.

As described above, in the flow illustrated in FIG. 30, preferably step S150 (count up of the counter 52X) and step S160 (determination of whether or not a count value of the counter 52X reaches the predetermined value) are performed from stopping of power supply from the battery 11 to the atomizer 22 until the determination period has elapsed. Preferably step S160 (for example, a process in which the replacement timing of the second cartridge 30 is notified) is also performed from stopping of power supply from the battery 11 to the atomizer 22 until the determination period has elapsed.

Other Embodiments

The present invention is described through the above-described embodiments, but it should not be understood that this invention is limited to the statements and the drawings constituting a part of this disclosure. From this disclosure, various alternative embodiments, examples, and operational technologies will be obvious to those skilled in the art.

In the embodiment, the first cartridge 20 has the end cap 25, but the embodiment is not limited thereto. For example, the first cartridge 20 may not have the end cap 25 when the reservoir 21 has a configuration (for example, a tank) in which it is possible to suppress leakage of the aerosol source 21A. In such a case, the aerosol flow adjustment chamber G is formed between the downstream end portion of the flow path forming body 23 and the upstream end portion of the flavor source container 31.

In the embodiment, the second cartridge 30 is accommodated in the first cartridge 20 (protruding portion 25E), but the embodiment is not limited thereto. For example, the power source unit 10 may accommodate the first cartridge 20 and the second cartridge 30. Alternatively, the first cartridge 20 and the second cartridge 30 may be connected at end surfaces to face each other. In such a case, for example, the first cartridge 20 and the second cartridge 30 are connected by screwing.

Although not particularly mentioned in the embodiment, preferably the end cap 25 is joined to the reservoir 21 to suppress refilling and the like of the aerosol source 21A in the reservoir 21.

In the embodiment, the end cap 25 has the protruding portion 25E that protrudes from the outer edge of the end cap 25 to the downstream side (flavor source container 31 side)

in the cross section orthogonal to the aerosol flow path (predetermined direction A). However, the embodiment is not limited thereto. Note that, when the end cap 25 is not provided, the flow path forming body 23 may have the protruding portion 25E that protrudes from the outer edge of the flow path forming body 23 to the downstream side (flavor source container 31 side) in the cross section orthogonal to the aerosol flow path (predetermined direction A). The protruding portion 25E contacts the upstream end portion of the flavor source container 31 (for example, the outer edge of the upstream end portion).

In the embodiment, a case is exemplified in which the atomizer 22 has a heating wire (coil) wound at a predetermined pitch. However, the embodiment is not limited thereto. The shape of the heating wire forming the atomizer 22 is arbitrary.

In the embodiment, a case is exemplified in which the atomizer 22 is configured by the heating wire. However, the embodiment is not limited thereto. The atomizer 22 may atomize the aerosol source 21A using ultrasonic waves.

In the embodiment, the first cartridge 20 is replaceable. However, the embodiment is not limited thereto. Specifically, in place of the first cartridge 20, an atomizing unit that has the reservoir 21 and the atomizer 22 may be provided in the non-burning type flavor inhaler 1, and the atomizing unit may be a unit that is not replaced.

In the embodiment, the second cartridge 30 is replaceable. However, the embodiment is not limited thereto. Specifically, in place of the second cartridge 30, the flavor source unit that has the flavor source 31A may be provided in the non-burning type flavor inhaler 1, and the flavor source unit may be a unit that is not replaced. However, the second cartridge 30 is not necessarily an essential feature.

In the embodiment, the first cartridge 20 and the second cartridge 30 are replaceable. However, the embodiment is not limited thereto. Specifically, a configuration having the first cartridge 20 and the second cartridge 30 may be provided in the non-burning type flavor inhaler 1.

In the embodiment, the package 300 has one first cartridge 20. However, the embodiment is not limited thereto. The package 300 may have two or more first cartridges 20.

In the embodiment, the power controller 53 controls the amount of power supplied from the battery 11 to the atomizer 22 by pulse control. However, the embodiment is not limited thereto. The power controller 53 may control the output voltage of the battery 11. In such a case, preferably the power controller 53 modifies (or corrects) the predetermined instruction such that the aerosol amount atomized by the atomizer 22 falls within the desired range accompanying the reduction of the accumulated amount in the battery 11. Specifically, the power controller 53 may increase the instruction voltage output to the battery 11 accompanying the reduction of the accumulated amount in the battery 11 as the modification of the predetermined instruction. The modification (or correction) of the output voltage of the battery 11 is realized using, for example, a DC/DC converter. The DC/DC converter may be a step-down converter, or may be a boost converter. Note that, the power controller 53 may control both pulse control and output voltage such that the aerosol amount atomized by the atomizer 22 falls within the desired range.

In the embodiment, the power controller 53 increases the duty ratio output to the battery 11 in one puff action accompanying the reduction of the accumulated amount in the battery 11 as the modification of the predetermined instruction. However, the embodiment is not limited thereto. The power controller 53 may extend the predetermined period for stopping power supply from the battery 11 to the atomizer 22 accompanying the reduction of the accumulated amount in the battery 11 as the modification of the predetermined instruction.

In the embodiment, the detector 51 is connected to a voltage sensor provided on a sensor line that connects the battery 11 and the atomizer 22, and detects power supply based on the output result of the voltage sensor. However, the embodiment is not limited thereto. For example, the detector 51 may be connected to a current sensor provided on the sensor line that connects the battery 11 and the atomizer 22, and may detect power supply based on the output result of the current sensor.

In the embodiment, the power controller 53 instructs, to the battery 11, output of power to the atomizer 22 in the puff period in which the puff action is performed, but does not instruct, to the battery 11, output of power to the atomizer 22 in the non-puff period in which the puff action is not performed. However, the embodiment is not limited thereto. The power controller 53 may switch power output to the atomizer 22 according to the operation of the hardware interface (for example, the switch or the button) for performing power output to the atomizer 22. That is, the puff action and the non-puff action are switched according to the operation of the hardware interface.

INDUSTRIAL APPLICABILITY

It is possible to provide a non-burning type flavor inhaler and a package that are able to improve convenience for the user by notifying to the user a replacement timing of a first cartridge or a replacement timing of a second cartridge.

The invention claimed is:

1. A cartridge for a non-burning type flavor inhaler comprising:
    a flow path forming body having a shape extending along a predetermined direction to form an aerosol flow path;
    an outer frame having a shape extending along the predetermined direction to accommodate the flow path forming body;
    a reservoir that is configured to retain an aerosol source, is positioned on the periphery of the flow path forming body in a cross section orthogonal to the predetermined direction and is positioned in a gap between the flow path forming body and the outer frame; and
    an end cap that closes the gap from a downstream side, wherein an outer edge of the end cap contacts an inner wall surface of the outer frame in the cross section orthogonal to the predetermined direction; and
    wherein an inner edge of the end cap is positioned between the outer edge of the flow path forming body and the inner edge of the flow path forming body in the cross section orthogonal to the predetermined direction.

2. The cartridge for a non-burning type flavor inhaler according to claim 1, wherein the end cap comprises a protruding portion that protrudes from the outer edge of the end cap.

3. The cartridge for a non-burning type flavor inhaler according to claim 1, wherein the end cap comprises a protruding portion that protrudes from the outer edge of the end cap to the upstream.

4. The cartridge for a non-burning type flavor inhaler according to claim 1, wherein the outer frame comprises a space capable of accommodating a part of another cartridge downstream of the end cap, and
    wherein an aerosol flow adjustment chamber that adjusts the flow of the aerosol supplied from the flow path of the flow path forming body to the other cartridge is formed in a part of the space between the end cap and the other cartridge in a state in which the other cartridge is inserted in the outer frame.

5. The cartridge for a non-burning type flavor inhaler according to claim 4, wherein the other cartridge includes a flavor source.

6. The cartridge for a non-burning type flavor inhaler according to claim 1, wherein the outer frame comprises a space capable of accommodating a part of another cartridge downstream of the end cap.

7. The cartridge for a non-burning type flavor inhaler according to claim 6, wherein the other cartridge includes a flavor source.

* * * * *